(12) United States Patent
Mercola et al.

(10) Patent No.: US 6,982,145 B1
(45) Date of Patent: *Jan. 3, 2006

(54) ISOLATION AND IDENTIFICATION OF CONTROL SEQUENCES AND GENES MODULATED BY TRANSCRIPTION FACTORS

(76) Inventors: Daniel Mercola, P.O. Box 3752, Rancho Santa Fe, CA (US) 92067; Eileen Adamson, P.O. Box 3752, Rancho Santa Fe, CA (US) 92067; Ian de Belle, 3158 Via Alicante, Apt. D, La Jolla, CA (US) 92037

( * ) Notice: Subject to any disclaimer, the term of this patent is extended or adjusted under 35 U.S.C. 154(b) by 585 days.

This patent is subject to a terminal disclaimer.

(21) Appl. No.: 10/032,260

(22) Filed: Dec. 20, 2001

Related U.S. Application Data

(63) Continuation-in-part of application No. 09/270,391, filed on Mar. 16, 1999, now Pat. No. 6,410,233.

(51) Int. Cl.
ㅤ*C12Q 1/68* (2006.01)
(52) U.S. Cl. .......................... 435/6; 435/7.1; 435/91.2; 536/23.1
(58) Field of Classification Search .................. 435/6, 435/7.1, 91.2; 536/25.4
See application file for complete search history.

(56) References Cited

U.S. PATENT DOCUMENTS 6,410,233 B2 * 6/2002 Mercola et al. ................ 435/6

OTHER PUBLICATIONS de Belle et al. (BioTechniques 29: 162-169, Jul. 2000).*
Orlando et al. (Cell, vol. 75, 1187-1198, Dec. 1993).*
Hallahan et al. (The Journal of Biological Chemistry, vol. 270, No. 51, p. 30303-30309).*

* cited by examiner

*Primary Examiner*—Juliet C. Switzer
(74) *Attorney, Agent, or Firm*—David B. Waller & Associates

(57) ABSTRACT

The present invention provides methods and compositions for isolating a nucleic acid molecule fragment comprising at least a portion of a gene, comprising: stimulating at least one cell or at least one nucleus with radiation; cross-linking at least one transcription factor to a nucleic acid molecule in said at least one cell or at least one nucleus with formaldehyde, forming at least one transcription factor-nucleic acid molecule complex; fragmenting said nucleic acid molecule to form at least one transcription factor-nucleic acid molecule fragment complex; and isolating the nucleic acid molecule fragment from said at least one transcription factor-nucleic acid molecule fragment complex to form at least one isolated nucleic acid molecule fragment; wherein said at least one isolated nucleic acid molecule fragment comprises at least a portion of the first exon of a gene whose expression is modulated by said transcription factor; further wherein said at least one isolated nucleic acid molecule fragment comprises at least one transcription factor binding site that is operably linked or in close proximity to said first exon of a gene.

10 Claims, 15 Drawing Sheets

FIG. 11

Clone 1 nucleotide sequence

```
TAATACGACTCACTATAGGGAGACGAGCGGTGTCATGGCCGCCGACAGTGACG
ATGGCGCAGTTTCAGCTCCCGCAGCTTCCGACGGTGGTGTCAGCAAAAGCACA
ACATCTGGGGAGGAGCTAGTAGTCCAGGTTCCCGTAGTGGATGTGCAAAGCAA
CAACTTCAAGGAGATGTGGCCATCCCTCCTGCTAGCCATAAAGACAGCTAATTT
CGTTGGCTGTGGACACGGAGCTGAGTGGGCTTGGGGACAAGAAGAGTTTGCT
GAACCAGTGCATTGAGGAACGTTACAAGGCCGTGTGTCATGCTGCCAGGACCC
GTTCTATCCTTTCCCTGGGCCTCGCCTGCTTCAAGCGGCAGCCAGACAAGGGT
GAACATTCCTATCTGGCTCAAGTGTTCAATCTCACTCTGCTGTGCATGGAGGAG
TATGTCATAGAACCAAAGTCTGTGCAGTTCCTGATACAGCATGGCTTCAACTTC
AACCAGCAGTATGCCCAAGGCATCCCCTACCATAAGGGCAATGACAAGGG
TGATGAGAGCCAGAGCCAGTCAGTACGGACCCTATTCCTGGAGCTAA
TCCGAAGCCCGCCGGCCCCTGTTGCTACACAATGGCCTTATAGACTTG
GTGTTCCTGTACCAAAACTTCTATGCACACCTCCCTGAGAGTCTGGGA
ACCTTCACCGCTGACCTCTGTGAGATGTTCCCAGCAGGCATTTATGACAC
CAAATATGCTGCTGAGTTTCATGCCCGTTTCGTGGCCTCCTACTTAGAATATGC
CTTCCGGAAATGTGTTTTAGGTGCTGAGGATTCAGCAGTGAACAAAACAGACC
ACAAAACCCTGCTCTTATGGAGCTTATATGCTAGTGGACCATTACCCTCTTGCG
CTGTTGCAGTGAACGGGAAAATGGGAAGCAGCGGGCAGCTGGCAGCCCACAC
CTTACCCTGGAGTTCTGCAACTATCCTTCCAGCATGAGGGACCATATTGATTAC
CGCTGCTGCCTGCCCCCAGCAACCCACCGTCCTCATCCCACCAGCATCTGTGAC
AACTTCTCGGCTTATGGCTGGTGCCCCCTGGGACCACAGTGTCCTCAGTCTCAC
GATATTGACCCTATCATTGACACTGATGAGGCTGCGGCAGAGGACAAGCGGCG
ACGGCGACGACGTAGGGAAAAACGGAAGAGGGCTTTATTGAACCTACCGGGG
ACACAGACCTCTGGGGAAGCTAAGGATGGTCCTCCCAAGAAGCAGGTCTGTGG
GGATAGCATCAAGCCTGAAGAAACCGAGCAGGAGGTGGCTGCCGATGAAACT
AGGAACCTGCCTCACTCCAAGCAAGGCAACAAAAATGACTTAGAGATGGGGAT
TAAGGCAGCAAGGCCTGAAATAGCTGATAGAGCTACCTCAGAAGTGCCAGGGA
GCCAAGCCAGTCCTAACCCAGTGCCTGGGGGTGGATTGCACCGGGCTGGTTTT
GATGCCTTTATGACAGGTTATGTGATGGCCTATGTGGAAGTGAGCCAGGGACC
GCAACCCTGCAGCTCTGGACCCTGGCTCCCTGAATGCCACAATAAGGTATATTT
GAGTGGCAAAGCTGTACCCCTCACAGTGGCCAAGAGCCAGTTCTCTCGTTCCT
CCAAAGCCCACAATCAGAAGATGAAGCTCACTTGGGGCAGTAGCTGATGCAAC
TTCCACCTTGCTCTCAGGTGGAACAGAGGTATTTTGGGTCTCTCTAGCCTGAAA
TGTCATCCTCAACTGCTACTGAGTTTGGGGGAGGGGGAATGTCTTGACAGACA
TCACTGCATTGCCCTGGACCGCCTCCTTTATCCCAGTGTTTGAGGTACAAGTAA
GAAGGCTGACCAGCACCTGTAACACTGACTTTATTTTTAAGTCTGAAAATGTCTT
GGGAAAGTTTTACAAAAAAAAAAATCAACAGAAGCAAGTTATGAAAAAAAAAA
AAAAAAAAAACTCGAGGGGGGGCCCGGTACCCAATTCTCCCTATAGTGAGTCG
TATTA
```

| kDa | C | TOE1 |

97 —

66 —  — TOE1

TOE1 Protein sequence

MAADSDDGAVSAPAASDGGVSKSTTSGEELVVQVPVVDVQSNNFKEMWPSLLL
AIKTANFVAVDTELSGLGDRKSLLNQCIEERYKAVCHAARTRSILSLGLACFKRQ
PDKGEHSYLAQVFNLTLLCMEEYVIEPKSVQFLIQHGFNFNQQYAQGIPYHKGN
DKGDESQSQSVRTLFLELIRARRPLVLHNGLIDLVFLYQNFYAHLPESLGTFTADL
CEMFPAGIYDTKYAAEFHARFVASYLEYAFRKCERENGKQRAAGSPHLTLEFCN
YPSSMRDHIDYRCCLPPATHRPHPTSICDNFSAYGWCPLGPQCPQSHDIDLIIDTD
EAAAEDKRRRRRREKRKRALLNLPGTQTSGEAKDGPPKKQVCGDSIKPEETEQ
EVAADETRNLPHSKQGNKNDLEMGIKAARPEIADRATSEVPGSQASPNPVPGGG
LHRAGFDAFMTGYVMAYVEVSQGPQPCSSGPWLPECHNKVYLSGKAVPLTVAK
SQFSRSSKAHNQKMKLTWGSS

TOE1 DNA sequence agcttatattctaatggggacagaaaaggaataatgaacataagtaaattccataagatgttaggtgataaatattagca
taaaaagcaaaaattagaccaagaggggaaaaaaaagagtgccaaggtggggtttaatgttgcaattttaaagactgtgg
tcaaggtagacccaaagcattctaagtgagtgcaaaggccccaaggagggtgcctggtatgtctgtggtacagtaagtag
gtcaatgtggttagaatggaatgagatgggactgagtggtagaagaggtcagagaagtaaaccagatgaggtggggagag
gagggtcacaaagtaccttataggccattggagggatttggctgccacacccttgctcttagaaggcagtcctcttactacagcctt
gcaggtccagtgatccgggcaccatccgcctcatcccctcactatgctctagccaaggttgactgaatttagttgcttaaacacctc
aagtgtgtctgcccaccttggggcctcacacaatccatttcctctgtttggactcttttatgcttttacctaacaccttatcatttttcaag
tcttgactgaaatgtccaaatcaggtcccctcatcttatcctatcacatatttctgccttgtagctcttacctaatgtaattttacattacttt
gattctttccatcagtgtgtacttcctgaatttgactgtaaaaaacgacttgagtgcaaggactgattctcttgttgattggtgtgtgtcc
aaagtcagtgccaggtaaactgtacacaatagatacctgttaaatgaattaatgggatgggggatagtcaaaagagtttcccttttt
aggataggagaaatccaaagagtttttttattttttgtttttttttttgtttgtttgttttgttttagagacagtgtgtccctcactttgctgctct
gccactcaggctggagtgcaataagaacatggctcactgcagcctcgacctcctgggctcaagccatcctctcacctcagcctc
ctgtagctgggactacaggtgcgcaccaccatgcccaactaattttaattttcttttgtagagacaaggtttcactatgttgcccag
gctagtcttgaactcctagggtcaagcgatcctcccaccttggcctcctaagatgattacaggccataagccactgcgcccggcc
caagcagttctgaataatgatgaaatgggctcagttgagagaagctgaagattaactataaacaatgagtaacaaaggagcactg
gaaggcagaggtggatgggaatcgtagtgtttacggagggactagtctccaataggaatttttttttttttttttttttgagacggagtt
tcgctcttgttgcctaggctgaagtgcaaaatggcgtgatctcggctcaccgcaacctctgcctcccaggttcaagcgattctcctg
cctcagcctcccaagtagtgggattacaggcgcccgcaccatacccagctaatttttttgtactttagtagagacggggtttcacc
atgttggccaggctggttttgaactccggacctcaggtaatccgcccgcctcggcctcccaaagtgctgggattacaggcgtga
gccaccgcgcccggcctaggaacctcttcaaattcaatcaccctctaggtcgactataccgcctagctgcttcacaatttgtccct
tcctcgccatccatactgccagccttaattcaagttcacattatcacttgattggattattacaaaagcttccctaccaatcggtcgctc
ttacaccctgggcagcctcctccgatggcccactccccgcctctttcactttctggagatcactgagctctccatcctctctgggaat
ttaccgatgcccagaacgccttctttcccccacacgaccctctcctagtctaactcctgggcgtgctttaagctcagctcaggca
gcgtcaccttctctggaaagcccaaacccagccaccccactacccgctacccgcggcccacgctgatgaagacagcagaac
acggaggccccgcgttcccgccgcgagagcaggagagaaagattacctcccgcgagctctagcgcgcccggctttccggc

FIG. 14 Cont.

gcactccaggggggcgtggctcgggtccacccgggctgcgagccggcagcacaggccaataggcaattagcgcgcgccagg
ctgccttccccgcgccggacccgggacgtctgaacggaagttcgacccatcggcgacccgacggcgagaccccgccccat
ccccgactgcctgaaccgcgccaggagacggaccgcaagtccagcgtacccacagacgactcaggcgggagacgagcggt
gtcATGGCCGCCGACAGTGACGATGGCGCAGTTTCAGCTCCCGCAGCTTCCGA
CGGTGGTGTCAGCAAAAGCACAACATCTGGGGAGGAGCTAGTAGTCCAGGTT
CCCGTAGTGGATGTGCAAAGCAACAACTTCAAGGAGATGTGGCCATCCCTCC
TGCTAGCCATAAAGACAGCTAATTTCGTGGCTGTGGACACGGAGCTGAGTGG
GCTTGGGGACAGGAAGAGTTTGCTGAACCAGTGCATTGAGGAACGTTACAAG
GCCGTGTGTCATGCTGCCAGGACCCGTTCTATCCTTTCCCTGGGCCTCGCCTG
CTTCAAGCGGCAGCCAGACAAGGGTGAACATTCCTATCTGGCTCAAGTGTTC
AATCTCACTCTGCTGTGCATGGAGGAGTATGTCATAGAACCAAAGTCTGTGC
AGTTCCTGATACAGCATGGCTTCAACTTCAACCAGCAGTATGCCCAAGGCAT
CCCCTACCATAAGGGCAATGACAAGGGTGATGAGAGCCAGAGCCAGTCAGT
ACGGACCCTATTCCTGGAGCTAATCCGAGCCCGCCGGCCCCTGGTGCTACAC
AATGGCCTTATAGACTTGGTGTTCCTGTACCAGAACTTCTATGCACACCTCCC
TGAGAGTCTGGGAACCTTCACCGCTGACCTGTGTGAGATGTTCCCAGCAGGC
ATTTATGACACCAAATATGCTGCTGAGTTTCATGCCCGTTTCGTGGCCTCCTA
CTTAGAATATGCCTTCCGGAAATGTGAACGGGAAAATGGGAAGCAGCGGGC
AGCTGGCAGCCCACACCTTACCCTGGAGTTCTGCAACTATCCTTCCAGCATGA
GGGACCATATTGATTACCGCTGCTGCCTGCCCCCAGCAACCCACCGTCCTCAT
CCCACCAGCATCTGTGACAACTTCTCGGCTTATGGCTGGTGCCCCTGGGACC
ACAGTGTCCTCAGTCTCACGATATTGACCTTATCATTGACACTGATGAGGCTG
CGGCAGAGGACAAGCGGCGACGGCGACGACGTAGGGAAAAACGGAAGAGG
GCTTTATTGAACCTACCGGGGACACAGACCTCTGGGGAAGCTAAGGATGGTC
CTCCCAAGAAGCAGGTCTGTGGGGATAGCATCAAGCCTGAAGAAACCGAGC
AGGAGGTGGCTGCCGATGAAACTAGGAACCTGCCTCACTCCAAGCAAGGCA
ACAAAAATGACTTAGAGATGGGGATTAAGGCAGCAAGGCCTGAAATAGCTG
ATAGAGCTACCTCAGAAGTGCCAGGGAGCCAAGCCAGTCCTAACCCAGTGCC
TGGGGGTGGATTGCACCGGGCTGGTTTTGATGCCTTTATGACAGGTTATGTGA
TGGCCTATGTGGAAGTGAGCCAGGGACCGCAACCCTGCAGCTCTGGACCCTG
GCTCCCTGAATGCCACAATAAGGTATATTTGAGTGGCAAAGCTGTACCCCTC
ACAGTGGCCAAGAGCCAGTTCTCTCGTTCCTCCAAAGCCCACAATCAGAAGA
TGAAGCTCACTTGGGGCAGTAGCTGA

US 6,982,145 B1

ISOLATION AND IDENTIFICATION OF CONTROL SEQUENCES AND GENES MODULATED BY TRANSCRIPTION FACTORS

REFERENCE TO RELATED APPLICATIONS

This application is a continuation-in-part application of patent application Ser. No.: 09/271,391 filed 16 Mar. 1999 now U.S. Pat. No.: 6,410,233.

This invention was made partially with government support awarded by the Public Health Service, National Institutes of Health Grant ROI CA 67888. The United States Government may have certain rights in the invention.

TECHNICAL FIELD

The present invention generally relates generally to the fields of molecular biology, in particular transcription factors and the identification of genes modulated by transcription factors.

BACKGROUND

Gene expression is modulated by proteins that bind to specific sequences in the control regions of genes. Once bound, these factors modulate transcription of the DNA into messenger RNA. A transcription factor typically influences the expression of several genes. By identifying these genes, the mechanisms of a cell's response during development, under stress conditions, or while undergoing tumorigenesis may be revealed and investigated.

In order to elucidate these mechanisms, it is necessary to identify the gene targets of the transcription factors that are active in the cell. A variety of methods have been utilized but most are indirect. For example, both subtraction cloning and differential RNA display can be used to obtain cDNAs of genes that are unique to a particular condition in which the transcription factors is present. The disadvantage of these methods is that the genes obtained may not be directly regulated by the transcription factor of interest. The genes mat be controlled by other transcription factors that are induced under the same conditions or that act downstream of the transcription factor of interest. Consequently, the genes identified in these methods may not be part of the regulatory program being investigated. Another process screens DNA arrays to identify the genes that hybridize to RNA prepared from cells which express a particular transcription factor but not to RNA isolated from cells which do not express the transcription factor. Unfortunately, this technique also may not lead to identification of genes under the direct regulation of the transcription factor.

To understand a modulated network, such as a signal transduction pathway, it is important to characterize as many of the genes that are being controlled by the transcription factor as possible. Unfortunately the procedure of isolating the genes from libraries has hindered progress toward identifying a set of genes regulated together by the transcription factor of interest. Screening cDNA libraries by hybridization to obtain genes corresponding to the DNA fragments obtained by a variety of methods requires that each fragment isolated be used individually to screen the library. This is extremely time-consuming, labor-intensive, and costly. Consequently there is a need in the industry to increase the efficiency of obtaining gene targets of transcription factors of interest.

BRIEF DESCRIPTION OF THE FIGURES

FIG. 11 depicts the complete sequence of a clone identified using the methods of the present invention (SEQ ID NO: 15) (Clone 1). Sequences used in gel-shift methods are in bold with a presumptive Egr-1 binding site in bold and italics. An open reading frame consisting of 702 base pairs is underlines. A presumptive TATA box (TTATAT) is also shown in bold.

FIG. 14 depicts the complete protein sequence (SEQ ID NO: 26) and DNA sequence (SEQ ID NO: 27) of TOEI identified using the methods of the present invention. The TOE1 5' sequence is shown in lower case letters and the cDNA sequences is shown in upper case letters.

SUMMARY

Figure 1:
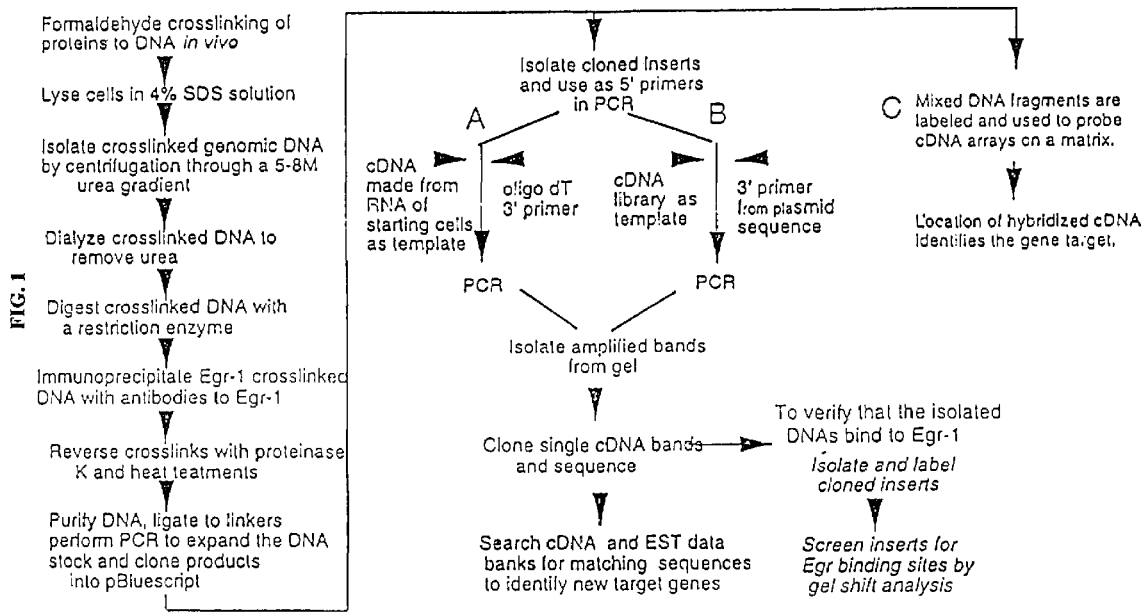
FIG. 1 depicts a schematic diagram of one aspect of the present invention.

The present invention recognizes that nucleotide sequences that regulate the expression of a gene can be identified by the binding of at least one transcription factor to at least a portion of a nucleotide sequence that regulates the expression of a gene. The present invention also recognizes that nucleotide sequences that encode at least a portion of a gene can be isolated, sequenced and characterized based on the binding of at least one transcription factor to a nucleotide sequence in close proximity to such nucleotide sequences that encode at least a portion of a gene.

One aspect of the present invention is A method for isolating a nucleic acid molecule fragment comprising at least a portion of a gene, comprising: stimulating at least one cell or at least one nucleus with radiation; cross-linking at least one transcription factor to a nucleic acid molecule in said at least one cell or at least one nucleus with formaldehyde, forming at least one transcription factor-nucleic acid molecule complex; fragmenting said nucleic acid molecule to form at least one transcription factor-nucleic acid molecule fragment complex; and isolating the nucleic acid molecule fragment from said at least one transcription factor-nucleic acid molecule fragment complex to form at least one isolated nucleic acid molecule fragment; wherein said at least one isolated nucleic acid molecule fragment comprises at least a portion of the first exon of a gene whose expression is modulated by said transcription factor; further wherein said at least one isolated nucleic acid molecule fragment comprises at least one transcription factor binding site that is operably linked or in close proximity to said first exon of a gene. The nucleic acid molecule is preferable DNA and the transcription factor can be any transcription factor known in the art or later identified. The cell can be any cell, such as a living or dead eukaryotic or prokaryotic cell. The isolated nucleic acid molecule fragment can be amplified, cloned and sequenced using appropriate methods. Such sequences can be compared to databases of sequences such as they are known in the art or later developed to identify novel genes. The at least one isolated nucleic acid molecule fragment, or a product or portion thereof, can be linked to a detectable label and be used as a probe to screen at least one immobilized nucleic acid molecule, such as on a nucleic acid molecule array.

Another aspect of the present invention is a method for isolating at least one nucleic acid molecule fragments that comprises a portion of a gene regulated by a transcription factor, comprising: cross-linking at least one transcription factor to at least one nucleic acid molecule in at least one cell or at least one nucleus, forming at least one transcription factor-nucleic acid molecule complex; fragmenting said at least one nucleic acid molecule to form at least one transcription factor-nucleic acid molecule fragment complex; and isolating at least one nucleic acid molecule fragment from said at least one transcription factor-nucleic acid molecule fragment complex to obtain at least one isolated nucleic acid molecule fragment; wherein said at least one isolated nucleic acid molecule fragment comprises at least a portion of the first exon of a gene whose expression is modulated by said transcription factor; further wherein said at least one isolated nucleic acid molecule fragment comprises at least one transcription factor binding site that is operably linked or in close proximity to said first exon of a gene. The nucleic acid molecule is preferable DNA and the transcription factor can be any transcription factor known in the art or later identified. The cell can be any cell, such as a living or dead eukaryotic or prokaryotic cell. The isolated nucleic acid molecule fragment can be amplified, cloned and sequenced using appropriate methods. Such sequences can be compared to databases of sequences such as they are known in the art or later developed to identify novel genes. The at least one isolated nucleic acid molecule fragment, or a product or portion thereof, can be linked to a detectable label and be used as a probe to screen at least one immobilized nucleic acid molecule, such as on a nucleic acid molecule array.

Still another aspect of the present invention is a method for identifying one or more cDNA molecules that correspond to one or more genes regulated by a transcription factor, comprising: cross-linking at least one transcription factor to at least one nucleic acid molecule in at least one cell or at least one nucleus, forming one or more transcription factor-nucleic acid molecule complexes; fragmenting said at least one nucleic acid molecule to form one or more transcription factor-nucleic acid molecule fragment complexes; isolating one or more nucleic acid molecule fragments from said one or more transcription factor-nucleic acid molecule fragment complexes to form one or more isolated nucleic acid molecule fragments; combining said one or more isolated nucleic acid molecule fragments with either: a cDNA library, or cDNA obtained by reverse transcription of a population of RNA molecules, to form a mixture comprising isolated nucleic acid molecule fragment/cDNA complexes; and amplifying one or more cDNAs that binds with said one or more isolated nucleic acid molecule fragment using said one or more nucleic acid molecule fragments as primers to obtain one or more isolated cDNA molecules, said one or more isolated cDNA molecules comprising at least a portion of a gene operably linked to or in close proximity to a nucleic acid sequence that binds with at least one transcription factor; and identifying said one or more cDNAs by either: sequencing said one or more cDNAs and comparing said sequence to the sequences of DNA molecules of known sequence, or hybridizing said one or more cDNAs to one or more nucleic acid molecules corresponding to known genes or nucleic acid sequences. The nucleic acid molecule is preferably DNA and the transcription factor can be any transcription factor known in the art or later identified. The cell can be any cell such as a living or dead eukaryotic or prokaryotic cell. The isolated nucleic acid molecule fragment or isolated cDNA molecule can be sequenced and compared to databases of sequences such as they are known in the art or later developed to identify novel genes. The isolated nucleic acid molecule fragment or isolated cDNA molecule can also be amplified using appropriate methods, such as PCR, and linked to a detectable label. Preferably, the isolated cDNA molecule is amplified using the isolated nucleic acid molecule fragment as a primer, such as a 3' primer or a 5' primer, more preferably as a 5' primer. The isolated nucleic acid molecule fragment or a portion thereof, or the isolated cDNA molecule or a portion thereof, can also be used as a probe to screen at least one immobilized nucleic acid molecule, such as on a nucleic acid molecule array.

Yet another aspect of the present invention is A method for identifying one or more genes or DNA sequences regulated by a transcription factor, comprising: cross-linking at least one transcription factor to at least one nucleic acid molecule in at least one cell or at least one nucleus, forming one or more transcription factor-nucleic acid molecule complexes; fragmenting said at least one nucleic acid molecule to form one or more transcription factor-nucleic acid molecule fragment complexes; isolating one or more nucleic acid molecule fragments from said one or more transcription factor-nucleic acid molecule fragment complexes to obtain one or more isolated nucleic acid molecule fragments; hybridizing said one or more isolated nucleic acid fragments to a known complementary nucleic acid sequence in an array of sequences known to be complementary to previously identified nucleic acid molecules of known sequence; and identifying one or more genes or DNA sequences regulated by a transcription factor when said one or more genes or DNA sequences regulated by a transcription factor hybridizes to said one or more isolated nucleic acid fragments on said array. The nucleic acid molecule is preferable DNA and the transcription factor can be any transcription factor known in the art or later identified. The cell can be any cell, such as a living or dead eukaryotic or prokaryotic cell. The isolated nucleic acid molecule fragment can be amplified, cloned and sequenced using appropriate methods. Such sequences can be compared to databases of sequences such as they are known in the art or later developed to identify novel genes. The at least one isolated nucleic acid molecule fragment, or a product or portion thereof, can be linked to a detectable label and be used as a probe to screen at least one immobilized nucleic acid molecule, such as on a nucleic acid molecule array.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures in cell culture, chemistry, microbiology, molecular biology, cell science and cell culture described below are well known and commonly employed in the art. Conventional methods are used for these procedures, such as those provided in the art and various general references (Sambrook et al., Molecular Cloning: A Laboratory Manual, $2^{nd}$ edition, Cold Spring Harbor Press, Cold Spring Harbor, N.Y. (1989)). Where the term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

"Portion of a gene" as used herein refers to a nucleic acid sequence of at least 30 nucleotides in length wherein the sequence extends from the regulatory region of a gene by at least 20 nucleotides into the transcribed sequence. The nucleic acid molecule comprising a portion of a gene may be about 30 nucleotides in length and will generally not exceed 5000 nucleotides in length.

"Isolated polynucleotide" refers to a polynucleotide of genomic, cDNA, or synthetic origin, or some combination thereof, which by virtue of its origin, the isolated polynucleotide (1) is not associated with the cell in which the isolated polynucleotide is found in nature, or (2) is operably linked to a polynucleotide that it is not linked to in nature. The isolated polynucleotide can optionally be linked to promoters, enhancers, or other regulatory sequences using methods known in the art (Sambrook et al., supra, 1989).

"Isolated protein" refers to a protein derived from cDNA or recombinant RNA, of synthetic origin, or some combination thereof, which by virtue of its origin the isolated protein (1) is not associated with proteins normally found within nature, or (2) is isolated from the cell in which it normally occurs, or (3) is isolated and substantially free of other proteins from the same cellular source, for example, free of cellular proteins, or (4) is expressed by a cell from a different species, or (5) does not occur in nature by isolation procedures known in the art.

"Polypeptide" is used herein as a generic term to refer to native protein, fragments, or analogs thereof.

"Active fragment" refers to a fragment of a parent molecule, such as an organic molecule, nucleic acid molecule, or protein or polypeptide, or combinations thereof, that retains at least one activity or a substantial portion of the activity of the parent molecule.

"Naturally occurring" refers to the fact that an object can be found in nature. For example, a polypeptide or polynucleotide sequence that is present in an organism, including viruses, that can be isolated from a source in nature and which has not been intentionally modified by man in the laboratory is naturally occurring.

"Operably linked" refers to a juxtaposition wherein the components so described are in a relationship permitting them to function in their intended manner. For example, a control sequence operably linked to a coding sequence is ligated in such a way that expression of the coding sequence is achieved under conditions compatible with the control sequences.

"Control sequences" refer to polynucleotide sequences that effect the expression of coding and non-coding sequences to which they are ligated. The nature of such control sequences differs depending upon the host organism; in prokaryotes, such control sequences generally include promoter, ribosomal finding site, and transcription termination sequences; in eukaryotes, generally, such control sequences include promoters, enhancers and transcription termination sequences. The term control sequences is intended to include components whose presence can influence expression, and can also include additional components whose presence is advantageous, for example, leader sequences and fusion partner sequences.

"Polynucleotide" refers to a polymeric form of nucleotides of more than three bases in length, either ribonucleotides or deoxynucleotides or a modified form of either type of nucleotide. The term includes single and double stranded forms of DNA or RNA or a combination of both.

"Nucleic acid molecule" refers to a polymeric form of nucleotides of at least two bases in length, either ribonucleotides or deoxynucleotides or a modified form of either type of nucleotide. The term includes single and double stranded forms of DNA or RNA or a combination of both.

"Nucleotide" refers to a single nucleotide that can polymerize to form a polynucleotide or a nucleic acid molecule.

"Directly" in the context of a biological process or processes, refers to direct causation of a process that does not require intermediate steps, usually caused by one molecule contacting or binding to another molecule (the same type or different type of molecule). For example, molecule A contacts molecule B, which causes molecule B to exert effect X that is part of a biological process.

"Indirectly" in the context of a biological process or processes, refers to indirect causation that requires intermediate steps, usually caused by two or more direct steps. For example, molecule A contacts molecule B to exert effect X which in turn causes effect Y.

"Sequence homology" refers to the proportion of base matches between two nucleic acid sequences or the proportion of amino acid matches between two amino acid sequences. When sequence homology is expressed as a percentage, for example 50%, the percentage denotes the proportion of matches of the length of sequences from a desired sequence that is compared to some other sequence. Gaps (in either of the two sequences) maybe permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible pair matches (90%), and most preferably not less than 19 matches out of 20 possible base pair matches (95%).

"Selectively hybridize", "selective hybridizing", "hybridization" or "hybridizing" refers to at least two molecules that can detectably and specifically bind. For example, a molecule can be a polynucleotides, oligonucleotides and fragments thereof that selectively hybridize to target nucleic acid strands, under hybridization and wash conditions that minimize appreciable amounts of detectable binding to nonspecific nucleic acids. High stringency conditions can be used to achieve selective hybridization conditions as known in the art. Generally, the nucleic acid sequence homology between the polynucleotides, oligonucleotides, and fragments thereof and a nucleic acid sequence of interest will be at least 30%, and more typically and preferably of at least 40%, 50%, 60%, 70%, 80% or 90%.

Hybridization and washing conditions are typically performed at high stringency according to conventional hybridization procedures. Typical hybridization conditions and methods for screening plaque lifts and other purposes are known in the art (Benton and Davis, Science 196:180 (1978); Sambrook et al., supra, (1989)).

Two amino acid sequences are homologous if there is a partial or complete identity between their sequences. For example, 85% homology means that 85% of the amino acids are identical when the two sequences are aligned for maximum matching. Gaps (in either of the two sequences being matched) maybe permitted to maximize matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at least 5 (in standard deviation units) using the program ALIGN with the mutation data matrix and a gap penalty of 6 or greater (Dayhoff, in Atlas of Protein Sequence and Structure, National Biomedical Research Foundation, volume 5, pp. 101–110 (1972) and Supplement 2, pp. 1–10). The two sequences or parts thereof are more preferably homologous if their amino acids are greater than or equal to 30% identical when optimally aligned using the ALIGN program.

"Corresponds to" refers to a polynucleotide sequence that is homologous (for example is identical, not strictly evolutionarily related) to all or a portion of a reference polynucleotide sequence, or that a polypeptide sequence is identical to all or a portion of a reference polypeptide sequence. In contradistinction, the term "complementary to" is used herein to mean that the complementary sequence will hybridize to all or a portion of a reference polynucleotide sequence. For illustration, the nucleotide sequence TATAC corresponds to a reference sequence TATAC and is complementary to a reference sequence GTATA.

The following terms are used to describe the sequence relationships between two or more polynucleotides: "reference sequence," "comparison window," "sequence identity," "percentage of sequence identity," and "substantial identity." A reference sequence is a defined sequence used as a basis for a sequence comparison; a reference sequence can be a subset of a larger sequence, for example, as a segment of a full length cDNA or gene sequence given in a sequence listing, or may comprise a complete cDNA or gene sequence. Generally, a reference sequence is at least 20 nucleotides in length, frequently at least 25 nucleotides in length, and often at lease 50 nucleotides in length. Since two polynucleotides can each (1) comprise a sequence (for example a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A comparison window, as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window can comprise additions and deletions (for example, gaps) of 20 percent or less as compared to the reference sequence (which would not comprise additions or deletions) for optimal alignment of the two sequences. Optimal alignment of sequences for aligning a comparison window can be conducted by the local homology algorithm (Smith and Waterman, Adv. Appl. Math., 2:482 (1981)), by the homology alignment algorithm (Needleman and Wunsch, J. Mol. Bio., 48:443 (1970)), by the search for similarity method (Pearson and Lipman, Proc. Natl. Acid. Sci. U.S.A. 85:2444 (1988)), by the computerized implementations of these algorithms such as GAP BESTFIT, FASTA and TFASTA (Wisconsin Genetics Software Page Release 7.0, Genetics Computer Group, Madison, Wis.), BLAST (http://ncbi.nlm.nih.gov/BLAST (Mar. 7, 1999) and Altschul et al., Nucleic Acids Res. 25:3389–3402 (1997) or by inspection. Preferably, the best alignment (for example, the result having the highest percentage of homology over the comparison window) generated by the various methods is selected.

"Sequence identity" means that two polynucleotide sequences are identical (for example, on a nucleotide-by-nucleotide basis) over the window of comparison.

"Percentage of sequence identity" is calculated by comparing two optimally aligned sequences over the window of comparison, determining the number of positions at which the identical nucleic acid base occurs in both sequences to yield the number of matched positions, dividing the number of matched positions by the total number of positions in the window of comparison (for example, the window size), and multiplying the result by 100 to yield the percentage of sequence identity.

"Substantial identity" as used herein denotes a characteristic of a polynucleotide sequence, wherein the polynucleotide comprises a sequence that has at least 30 percent sequence identity, preferably at least 50 to 60 percent sequence, more usually at least 60 percent sequence identity as compared to a reference sequence over a comparison window of at least 20 nucleotide positions, frequently over a window of at least 25 to 50 nucleotides, wherein the percentage of sequence identity is calculated by comparing the reference sequence of the polynucleotide sequence that may include deletions or additions which total 20 percent or less of the reference sequence over the window of comparison. "Substantial identity" as applied to polypeptides herein means that two peptide sequences, which optimally aligned, such as by the programs GAP or BESTFIT using default gap weights, share at lease 30 percent sequence identity, preferably at least 40 percent sequence identity, and more preferably at least 50 percent sequence identity, and most preferably at least 60 percent sequence identity. Preferably, residue positions, which are not identical, differ by conservative amino acid substitutions.

"Identifying" as used herein refers to the determination of the identity of a nucleic acid sequence by comparison, or matching, of the sequence to known nucleic acid sequences having substantial identity to the nucleic acid sequence identified using the methods of the present invention. In addition, the act of "identifying" may include the performance of particular assays such as for example a hybridization assay.

"Fragment" as used herein for a protein, peptide or polypeptide is a portion of the parent molecule. Fragment as used herein for a nucleic acid molecule is a portion of the parent molecule.

"Active fragment" as used herein for a protein, peptide or polypeptide is a fragment of a parent molecule that retains at least one activity of the parent protein, peptide or polypeptide. Active fragment as used herein for a nucleic acid molecule is a fragment that retains at least one activity of the parent nucleic acid molecule. An active fragment of a nucleic acid molecule also refers to a fragment of a nucleic acid molecule that encodes a protein, peptide or polypeptide having at least one activity of the full-length protein.

"Conservative amino acid substitutions" refer to the interchangeability of resides having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagines and glutamine; a group of amino acids having aromatic side chains is phenylalanine, tyrosine and tryptophan; a group of amino acids having basic side chains is lysine, arginine and histidine; a group of amino acids having sulfur-containing side chains is cysteine and methionine. Some preferred conservative amino acid substitution groups are: valine-leucine-isoleucine; phenylalanine-tyrosine; lysine-arginine; alanine-valine; glutamic acid-aspartic acid; and asparagine-glutamine.

"Modulation" or "modulated" refers to the capacity to either enhance or interfere with a functional property of a biological activity or process, for example, but not limited to, enzyme activity transcription factor activity or receptor binding. Such enhancement or interference may be contingent on the occurrence of a specific event, such as activation of a signal transduction pathway and/or may be manifest only in particular cell types.

"Modulator" refers to a chemical (naturally occurring or non-naturally occurring), such as a biological macromolecule (for example, nucleic acid, protein, non-peptide of organic molecule) or an extract made from biological materials, such as prokaryotes, bacteria, eukaryotes, plants, fungi, multicellular organisms or animals, invertebrates, vertebrates, mammals and humans, including, where appropriate, extracts of: whole organisms or portions of organisms, cells, organs, tissues, fluids, whole cultures or portions of cultures, or environmental samples or portions thereof that alters the activity of a biological process or molecule, such as, for example a receptor, enzyme or transcription factor. Modulators are typically evaluated for potential activity to enhance or interfere with (directly or indirectly) a biological process or processes (for example, agonist, partial agonist, antagonist, partial antagonist, antineoplastic agent, cytotoxins, inhibitors of neoplastic transformation or cell proliferation, cell proliferation promoting agents, antiviral agents, antimicrobial agents, antibacterial agents, antibiotics, and the like) by inclusion in assays described herein. The activity of a modulator may be known, unknown or partially known.

"Label" or "labeled" refers to incorporation of a detectable marker, for example by incorporation of a radiolabled compound or attachment to a polypeptide of moieties such as biotin that can be detected by the binding of a section moiety, such as marked avidin. Various methods of labeling polypeptide, nucleic acids, carbohydrates, and other biological or organic molecules are known in the art. Labels can be radioactive, fluorescent, chromagenic, chemiluminescent, or have other readouts or properties known in the art or later developed. Detection can be based on enzymatic activity, such as beta-galactosidase, beta-lactamase, horseradish peroxidase, alkaline phosphatase, luciferase; radioisotopes such as $^{3}H$, $^{14}C$, $^{35}S$, $^{125}I$ or $^{131}I$); fluorescent proteins, such as green fluorescent proteins; or other fluorescent labels, such as FITC, rhodamine, and lanthanides. Where appropriate, these labels can be the product of the expression of reporter genes, as that term in understood in the art. Examples of reporter genes are beta-lactamase (U.S. Pat. No. 5,741,657 to Tsien et al., issued Apr. 21, 1998) and green fluorescent protein (U.S. Pat. No. 5,777,079 to Tsien et al., issued Jul. 7, 1998; U.S. Pat. No. 5,804,387 to Cormack et al., issued Sep. 8, 1998).

As used herein a nucleic acid molecule "encodes" a polypeptide if transcription of the nucleic acid molecule and translation of the mRNA produce the polypeptide. Thus, nucleic acid molecules of the present invention include those whose nucleotide sequence encodes a polypeptide directly, such as cDNA, or whose nucleotide sequence includes introns that are spliced out by following transcription into mRNA, such as genomic DNA. It also includes nucleic acid molecules having sequences that are degenerate versions of any of the aforementioned nucleotide sequences.

"Transcription factor" means a molecule that can modulate the expression or transcription of a gene or nucleic acid sequence. Such transcription factors are known in the art, such as those described in http://transfac.gbf-braunschweig.de/TRANSFAC/c1/c1.html (Feb. 17, 1999). Transcription factors include, but are not limited to, leucine zipper factors, helix-loop-helix factors, helix-loop-helix/leucine zipper factors, NF-1 factors, RF-X factors, bHSH factors, Cys4 zinc finger of nuclear receptor factors, diverse Cys-4 zinc finger factors, Cys2His2 zinc finger factors, Cys6 cysteine-zinc cluster factors, Homeo domain factors, paired box factors, fork head/winged helix factors, heat shock factors, tryptophane cluster factors, TEA domain factors, RHR factors, p53 factors, MADS box factors, beta-barrel alpha-helix factors, TATA-binding factors, HMG factors, heteromeric CCAAT factors, Grainyhead factors, cold-shock domain factors, Runt factors, copper fist factors, HMGI(Y) factors, STAT factors and pocket domain factors.

"In close proximity" means within between about 0 and about 1,000 nucleotide bases, preferably within between about 10 and about 750 nucleotide bases or within between about 20 and about 500 nucleotide bases, more preferably within between about 30 and about 300 nucleotide bases or with between about 40 and about 200 nucleotide bases, and most preferably within between about 50 and about 100 nucleotide bases of a nucleotide that binds with a transcription factor.

Other technical terms used herein have their ordinary meaning in the art that they are used, as exemplified by a variety of technical dictionaries, such as the McGraw-Hill Dictionary of Chemical Terms and the Stedman's Medical Dictionary.

The present invention recognizes that nucleotide sequences that regulate the expression of a gene can be identified by the binding of transcription factors to such sequences. Such sequences and genes that are regulated by such transcription factors, can be isolated, sequenced and characterized.

As a non-limiting introduction to the breadth of the present invention, the present invention includes several general and useful aspects, including:

One aspect of the present invention is a method for isolating at least one nucleic acid molecule comprising at least a portion of a gene, including: cross-linking at least one transcription factor to a nucleic acid molecule in at least one cell or at least one nucleus, forming at least one transcription factor/nucleic acid molecule complex; fragmenting the nucleic acid molecule to form at lease one transcription factor/nucleic acid molecule fragment; and isolating at least one nucleic acid molecule from said at least one transcription factor/nucleic acid molecule fragment to form at least one isolated nucleic acid molecule fragment; wherein said at least one isolated nucleic acid molecule fragment comprises at least a portion of the first exon of a gene whose expression is modulated by said transcription factor; further wherein said at lease one isolated nucleic acid molecule fragment comprises at lease one transcription factor binding site that is in close proximity to or operably linked to said first exon of a gene. The nucleic acid molecule is preferably DNA and the transcription factor can be any transcription factor known in the art or later identified. The cell can be any cell, such as a living or dead eukaryotic or prokaryotic cell. The isolated nucleic acid molecule fragment can be amplified, cloned and sequenced using appropriate methods. Such sequences can be compared to databases of sequences such as they are known in the art or later developed to identify novel genes. The at least one isolated nucleic acid molecule fragment, or a product or portion thereof, can be linked to a detectable label and be used as a probe to screen at least one immobilized nucleic acid molecule, such as on a nucleic acid molecule array.

Another aspect of the present invention is a method for isolating at least one nucleic acid molecule that can include at least a portion of a gene operably linked to or in close proximity to a nucleic acid sequence that binds with at least one transcription factor, comprising: cross-linking at least one transcription factor to a nucleic acid molecule in at least one cell or at least one nucleus, forming at least one transcription factor/nucleic acid molecule complex; fragmenting the nucleic acid molecule to form at least one transcription factor/nucleic acid molecule fragment; isolating at least one nucleic acid molecule fragment from said at least one transcription factor/nucleic acid molecule fragment to form at least one isolated nucleic acid molecule fragment; combining the at least one isolated nucleic acid molecule fragment with either: a cDNA library, or a cDNA derived from reverse transcription of a population of RNA molecules, to form a mixture comprising isolated nucleic acid molecule fragment/cDNA complexes; and isolating the cDNA that binds with the isolated nucleic acid molecule fragment to obtain at least one isolated cDNA molecule. The nucleic acid molecule is preferably DNA and the transcription factor can be any transcription factor known in the art or later identified. The cell can be any cell such as a living or dead eukaryotic or prokaryotic cell. The isolated nucleic acid molecule fragment or isolated cDNA molecule can be sequenced and compared to databases of sequences such as they are known in the art or later developed to identify novel genes. The isolated nucleic acid molecule fragment or isolated cDNA molecule can also be amplified using appropriate methods, such as PCR, and linked to a detectable label. Preferably, the isolated cDNA molecule is amplified using the isolated nucleic acid molecule fragment as a primer, such as a 3' primer or a 5' primer, more preferably as a 5' primer. The isolated nucleic acid molecule fragment or a portion thereof, or the isolated cDNA molecule or a portion thereof, or an amplified product or portion thereof can also be used as a probe to screen at least one immobilized nucleic acid molecule, such as on a nucleic acid molecule array.

These aspects of the present invention, as well as others described herein, can be achieved by using the methods, articles of manufacture and compositions of matter described herein and as they are known in the art. To gain a full appreciate of the scope of the present invention, it will be further recognized that various aspects of the present invention can be combined to make desirable embodiments of the invention.

I A Method for Identifying a Nucleic Acid Molecule Comprising at Least a Portion of a Gene One aspect of the present invention is a method for isolating at least one nucleic acid molecule comprising at least a portion of a gene, including: cross-linking at least one transcription factor to a nucleic acid molecule in at least one cell or at least one nucleus, forming at least one transcription factor/nucleic acid molecule complex; fragmenting the nucleic acid molecule to form at least one transcription factor/nucleic acid molecule fragment; and isolating at least one nucleic acid molecule from said at least one transcription factor/nucleic acid molecule fragment to form at least one isolated nucleic acid molecule fragment; wherein said at least one isolated nucleic acid molecule fragment comprises at least a portion of the first exon of a gene whose expression is modulated by said transcription factor; further wherein said at least one isolated nucleic acid molecule fragment comprises at least one transcription factor binding site that is in close proximity to or operably linked to said first exon of a gene. The nucleic acid molecule is preferably DNA and the transcription factor can be any transcription factor known in the art or later identified. The cell can be any cell, such as a living or dead eukaryotic or prokaryotic cell. The isolated nucleic acid molecule fragment can be amplified, cloned and sequenced using appropriate methods. Such sequences can be compared to databases of sequences such as they are known in the art or later developed to identify novel genes. The at least one isolated nucleic acid molecule fragment, or a product or portion thereof, can be linked to a detectable label and be used as a probe to screen at least one immobilized nucleic acid molecule, such as on a nucleic acid molecule array.

In practice, the present invention provides at least one transcription factor and at least one nucleic acid molecule. The transcription factor and the nucleic acid molecule are preferably in at least one cell or nucleus. The nucleic acid molecule can be any nucleic acid molecule, but is preferably genomic DNA.

The transcription factor can be any transcription factor as that term is known in the art. The transcription factor can be a known transcription factor, a presumptive transcription factor, or an unknown transcription factor. One preferred transcription factor of the present invention is Egr-1 and transcription factors that are similar to Egr-1 in sequence, function and binding affinities to target nucleic acid sequences.

A cell, such as a prokaryotic or eukaryotic cell, can be living or dead and be provided in a primary cell line, a continuous cell line, a clonal population of cells, or a biological sample, such as a tissue, organ, embryo, fluid or extract thereof. Eukaryotic organisms are preferred, such as yeast or multicellular organisms, such as invertebrates or vertebrates, such as, but not limited to test animals such as mice, rats, rabbits or monkeys, or human subjects. Nuclei isolated from prokaryotic and eukaryotic cells can also be used in the present invention. Such nuclei can be prepared using methods known in the art (see, Sambrook et al., supra, 1989).

The transcription factor binds to the nucleic acid molecule in order to modulate the expression of genes encoded by the nucleic acid molecule. Such binding may be, and usually is, reversible. The transcription factor-nucleic acid molecule complex is made substantially irreversible, preferably by cross-linking the transcription factor to the nucleic acid molecule. Such cross-linking can be accomplished by a variety of methods, such as by contacting or exposing the cell or nuclei to chemical or biological fixatives, such as ultraviolet irradiation (Graba et al., The EMBO Journal, 11:3375–3384 (1992)) or paraformaldehyde or formaldehyde (Deveaux et al., The EMBO Journal, 16:5654–5661 (1997) and Cohen-Kaminsky et al., The EMBO Journal 17:5151–5160 (1998) and Botquin et al., Genes and Development 12:2073–2090 (1998)). The duration and amount of radiation or chemical used to cross-link the transcription factor to the nucleic acid molecule can be readily determined by one skilled in the art using the methods of the present invention to confirm that such cross-linking has occurred. However, such cross-linking is not critical to the present invention (see, for example, Gould and White, Development, 116:1163–1174 (1992), Gould et al., Nature, 348: 308–312 (1990), Bigler and Eisenman, Mol. Ann Cell. Biol., 14:7621–7632 (1994), Grandori et al., The EMBO Journal, 15:4344–4357 (1996), and Bigler et al., The EMBO J. 14:5710–5723 (1995)).

The cell or nuclei are then lysed using methods known in the art to free the transcription factor-nucleic acid molecule complex from the cell or nucleus (Bigler et al., Mol. & Cell. Biol. 14:7621–7632 (1994); Gould et al., Nature, 348: 308–312 (1990); Grandori et al., EMBO J. 15:4344–4357 (1996) and Grabe at al., EMBO J. 11:3375–3384 (1992)). For example, cells or nuclei can be lysed using a variety of methods, such as detergent solutions, such as SDS, or by mechanical means, such as passage through a nozzle such as a needle, or by sonication. The transcription factor-nucleic acid molecule complexes in the sample can be isolated using a variety of methods known in the art, such as centrifugation through a gradient, such as urea or cesium chloride. The regions of the gradient containing the transcription factor-nucleic acid molecule complex are collected, and the compound or composition in the sample used to make the gradient, such as urea or cesium chloride, is preferably substantially removed by methods known in the art, such as dialysis, to prevent the compound or composition used in the gradient from substantially interfering with later reactions or steps.

The transcription factor-nucleic acid molecule complexes are preferably contacted with nucleases, such as endonucleases and/or exonucleases, in order to divide the nucleic acid molecule into fragments. In the alternative, such fragments can be obtained using chemicals that cleave nucleic acid molecules, such as a strong base or a strong acid, or by mechanical methods, such as passing the nucleic acid molecule through a nozzle such as a needle, or by sonication to shear a nucleic acid molecule. This procedure provides transcription factor-nucleic acid molecule fragment complexes.

The transcription factor-nucleic acid molecule fragment complexes are optionally isolated using methods known in the art, such as molecular sieve chromatography, density gradient centrifugation, affinity chromatography, affinity absorption (such as onto a solid phase, such as a plate or bead) or immunoprecipitation or a specific-binding reaction. Methods that utilize specific binding reactions can use receptor preparations, such as antibodies or active fragments thereof, such as the Fv region of an antibody, that specifically find with a transcription factor. Methods that utilize specific binding reactions are preferred because they result in a product that is of substantial purity. The receptor preparations can bind to a known transcription factor, a presumptive transcription factor, or be directed to a variety of cellular components. Preferably, the receptor is an antibody, which can be a monoclonal antibody.

The nucleic acid molecule fragment in the transcription factor-nucleic acid molecule fragment complex is isolated. Preferably, the transcription factor is removed using proteolytic digestion or treatment with protein denaturing agents, such as phenol, optionally with heat (de Belle et al., J. Cell. Biol. 141:355–348 (1998). The resulting nucleic acid molecule fragments are optionally separated from other components of the mixture using methods known in the art, such as dialysis, ethanol precipitation, electrophoresis or molecular sieve chromatography.

Preferably, the nucleic acid molecule fragments are attached to linker nucleic acid molecules using methods known in the art, such as blunt-end ligation or cohesive-end ligation of linkers. The choice of linkers and method of ligation depends on whether the nucleic acid molecule has blunt ends or cohesive ends as a result of the digestion of the nucleic acids in the transcription factor/nucleic acid molecule complex. Preferably, the linker nucleic acid molecules are chosen so that they can serve as 5' or 3' primers for nucleic acid molecule amplification procedures, such as polymerase chain reaction (PCR), and/or for cloning into vectors using methods known in the art (Sambrook et al., supra, 1989). If cloned into vectors, the nucleic acid molecule fragments can be amplified in a host cell appropriate for the vector. Such methods can result in a library of clones that comprise nucleic acid molecules that bind with a transcription factor and preferably at least a portion of at least one gene, such as a control sequence, 3' untranslated region, intron or exon. The vectors can also be used to amplify the nucleic acid molecule fragment using nucleic acid amplification procedures, such as PCR, using appropriate primers that correspond to the linkers. PCR primers generally comprise two nucleotide sequences, one with sense orientation and one with antisense orientation, employed under preferred conditions (see, Innis, PCR Strategies, Academic Press, San Diego, 1995). Alternately, mRNA derived from the vector can be reverse transcribed and be amplified using appropriate primers. The nucleic acid molecule fragments of the present invention can be isolated and/or amplified using a variety of methods, such as those described below.

In one aspect of the invention, linker nucleic acid molecules are ligated to at least one end of nucleic acid molecule fragment of the present invention. This nucleic acid molecule fragment is amplified using appropriate nucleic acid amplification procedures, such as PCR, using appropriate primers, such as those derived from the sequences of the linker nucleic acid molecules or the nucleic acid molecule fragment. The amplified nucleic acid molecule fragments optionally, but preferably, are cloned into a vector, such as a plasmid, to create a library of nucleic acid molecule fragments of the present invention. The vectors can be optionally digested using for example, at least one restriction enzyme, to remove the amplified nucleic acid molecule fragment from the vector. The vector or the removed amplified complex are isolated by, for example, gel electrophoresis, to obtain nucleic acid molecules including the nucleic acid molecule fragments of the present invention.

In another aspect of the present invention, linker nucleic acid molecules are ligated to at least one end of the nucleic acid molecule fragment of the present invention. This complex is amplified using appropriate nucleic acid molecule amplification procedures, such as PCR, using appropriate primers, such as those derived from the linker nucleic acid molecule's sequence. The linker nucleic acid molecules are removed from the amplification product using, for example, at least one appropriate restriction enzyme. The products of this reaction are separated using appropriate methods, such as gel electrophoresis, to obtain isolated nucleic acid molecule fragments of the present invention.

In a further aspect of the present invention, the nucleic acid molecule fragments of the present invention are clones into a vector, such as a plasmid, using appropriate methods. The vector is digested using, for example, at least one appropriate restriction enzyme. The products of this reaction are separated using, for example, gel electrophoresis, and the nucleic acid molecule fragments of the present invention isolated.

The nucleic acid molecule fragments of the present invention, their PCR products or their cloned counterparts optionally digested from a vector can be used in PCR reactions as described below. The nucleic acid molecule fragments of the present invention can also be used in hybridization reactions, such as screening nucleic acid molecule arrays, or be part of a nucleic acid molecule array. In this instance, the nucleic acid molecule fragments of the present invention are preferably linked to a detectable label.

The nucleotide sequence of the nucleic acid molecule fragments of the present invention can be determined using methods known in the art (Sambrook et al., supra, 1989). In addition to sequences that bind with a transcription factor, the nucleic acid molecule fragments of the present invention can be linked to at least a portion of an open reading frame of a gene. When the nucleotide sequence of the nucleic acid molecule fragments of the present invention are compared with databases of known nucleic acid sequences, such genes can be identified. If the sequences of the present invention are not known, then the present invention has identified at least a portion of a novel gene that is presumptively regulated by a transcription factor. If the transcription factor/nucleic acid molecule fragment was isolated using specific binding reactions, such as anti-transcription factor antibodies, then the identified gene is presumptively regulated by transcription factors that bind with such anti-transcription factor antibodies.

The nucleic acid molecule fragments isolated by the present invention can include sequences that bind with a transcription factor as well as regions that are in close proximity to regions or sequences that bind with a transcription factor. Not wishing to be limited to any mechanism, the inventors contemplate that the methods of the present invention result in nucleic acid molecule fragments that include regions cross-linked to transcription factors and regions that are not cross-linked to transcription factors. The regions that are not cross-linked to transcription factors are in close proximity to the regions that are cross-linked to transcription factors. Regions that are in close proximity to regions that are cross-linked to transcription factors can be upstream or downstream from the regions that bind with a transcription factor and can encode introns or exons. Thus, the methods of the present invention can isolate nucleic acids including introns or exons of a gene.

Preferably, an isolated nucleic acid molecule fragment of the present invention include at least a portion of the first exon of a gene that is regulated by at least one transcription factor. More preferably, the isolated nucleic acid molecule fragment of the present invention includes at least a portion of the control sequence of control sequences that bind with a transcription factor that modulates the transcription of the gene, which need not be operably linked to or in close proximity with the first exon of a gene that is regulated by at least one transcription factor. Preferably, the nucleic acid molecule fragment of the present invention includes at least a portion of the control sequence and at least a portion of the first exon on a gene that are operably linked or in close proximity to each other. Thus, the isolated nucleic acid molecule of the present invention comprises control sequences that modulate at least a portion of the first exon of a gene, at least a portion of an open reading frame, preferably the first exon of the open reading frame. Accordingly, the present invention identifies the appropriate gene whose transcription is modulated by a transcription factor.

For example, a region of a nucleic acid molecule that binds with a transcription factor can be within a gene, upstream of a gene or downstream of a gene. The isolation of a region that binds with a transcription factor can result in the isolation of a portion of a gene that is upstream or downstream from the region that binds with a transcription factor. The nucleic acid molecule fragments of the present invention can be optionally cloned or amplified using appropriate procedures, and the sequence of the nucleic acid molecule fragments obtained using established methods. These sequences can be compared to databases of known sequences. If the present invention isolates at least a portion of a gene having a known sequence, then that gene is presumptively modulated by the transcription factor. If the present invention isolates a nucleic acid molecule having a novel sequence, then the present invention has isolated at least a portion of a nucleic acid molecule that encodes a novel control sequence or a novel gene. Novel nucleic acid sequences identified by the present invention can be used as primers to isolate the novel gene.

Alternatively, the nucleic acid molecule fragments of the present invention or their amplification products, can be optionally linked to a detectable label and used to screen arrays of nucleic acids, such as those including cDNA libraries. The binding of a nucleic acid molecule fragment of the present invention to a member of such a nucleic acid molecule array identifies the cDNA that the nucleic acid molecule fragment of the present invention corresponds to.

II A Method for Isolating a Nucleic Acid Molecule that Includes at Least a Portion of a Gene Using a cDNA Molecule Another aspect of the present invention is a method for isolating at least one nucleic acid molecule that can include at least a portion of gene operably linked to or in close proximity to a nucleic acid sequence that binds with at least one transcription factor, comprising: cross-linking at least one transcription factor to a nucleic acid molecule in at least one cell or at least one nucleus, forming at least one transcription factor/nucleic acid molecule complex; fragmenting the nucleic acid molecule to form at least one transcription factor/nucleic acid molecule fragment; isolating at least one nucleic acid molecule fragment from said at least one transcription factor/nucleic acid molecule fragment to form at least one isolated nucleic acid molecule fragment; combining the at least one isolated nucleic acid molecule fragment with either: a cDNA library or a cDNA or cDNA population derived from reverse transcription of a population of RNA molecules, to form a mixture comprising isolated nucleic acid molecule fragment/cDNA complexes; and isolating the cDNA that binds with the isolated nucleic acid molecule fragment to obtain at least one isolated cDNA molecule. The nucleic acid molecule is preferably DNA and the transcription factor can be any transcription factor known in the art or later identified. The cell can be any cell such as a living or dead eukaryotic or prokaryotic cell. The isolated nucleic acid molecule fragment or isolated cDNA molecule can be sequenced and compared to databases of sequences such as they are known in the art or later developed to identify novel genes. The isolated nucleic acid molecule fragment or isolated cDNA molecule can also be amplified using appropriate methods, such as PCR, and linked to a detectable label. Preferably, the isolated cDNA molecule is amplified using the isolated nucleic acid molecule fragment as a primer, such as a 3' primer or a 5' primer, more preferable s a 5' primer. The isolated nucleic acid molecule fragment or a portion thereof, or the isolated cDNA molecule or a portion thereof, can also be used as a probe to screen at least one immobilized nucleic acid molecule, such as on a nucleic acid molecule array.

Nucleic acid molecules comprising the nucleic acid molecule fragments of the present invention can also be contacted with a cDNA library derived from a cell of choice. Preferably, the cell is the same cell used to make the nucleic acid molecule fragments of the present invention. More preferably, the cell used to make the cDNA library was subjected to the same conditions as the cell used to make the nucleic acid molecule fragments of the present invention so that the same nucleic acid molecules were transcribed. Such cDNA libraries can be made using methods known in the art, or purchased. Alternatively, a different cell, or a cell subjected to different conditions than the cell used to make the nucleic acid molecule fragments and cDNA libraries of the present invention can be used in order to identify genes that are expressed under different conditions. Such methods are known as array screening methods (see, for example, Iyer et al., Science 283:83–87 (1999)).

The binding of the nucleic acid molecule fragment of the present invention to a cDNA molecule can be used as the basis of a PCR reaction to amplify cDNA molecules that bind with a nucleic acid molecule fragment of the present invention. A cDNA library from a cell, preferable the cell that was used to produce the nucleic acid molecule of the present invention, cloned into a known site of a vector is preferably used as a template. The nucleic acid molecule of the present invention is used as a 5' PCR primer, and an appropriate 3' PCR primer is derived from vector sequences. Preferably, the 3' PCR primer is derived from vector sequences that are adjacent to the location where the cDNA ligates with the vector nucleic acid molecule.

Alternatively, the nucleic acid molecule of the present invention is used as a 3' PCR primer, and an appropriate 5' PCR primer is derived from vector sequences. Preferable, the 5' PCR primer is derived from vector sequences that are adjacent to the location where the cDNA ligates with the vector nucleic acids. PCR reactions are performed, such as cDNA molecules that hybridize with the 5' PCR primer are amplified. In some cases, the transcription factor-binding site may be within an intron or in the 3' untranslated region of a gene. This invention contemplates that PCR can also be used in this instance using the nucleic acid molecule fragments of the present invention as 3' primers and using sequences derived from the cDNA vector as 5' primers in amplification reaction.

The PCR products are isolated and cloned into an appropriate vector. These PCR amplified sequences can be compared to databases containing known nucleotide sequences in order to identify the gene that gave rise to the cDNA molecule. The identified gene is presumptively regulated by a transcription factor. If the transcription factor-nucleic acid molecule fragment was isolated using specific binding reactions, such as anti-transcription factor antibodies, then the identified gene is presumptively regulated by transcription factors that bind with such anti-transcription antibody.

The present invention includes a nucleic acid molecule comprising a nucleic acid molecule identified by the method of the present invention, such as SEQ ID NO: 15, exons thereof, protein coding regions thereof, control regions thereof, genes thereof, transcription factor binding regions thereof, sequences having substantial identity thereto, sequences having substantial homology thereto, and having between at least about 60% and about 99%, preferably between about 70% and about 95%, and most preferably between about 80% and about 90% homology to a nucleic acid molecule identified by the method of the present invention; and fragments or active fragments of any of the foregoing. The nucleic acid molecule of the present invention can be cloned into an appropriate vector, and the vector can be transfected or transformed into an appropriate host cell using methods established in the art to make transfected or transformed host cells (see, Sambrook et al., supra, 1989). The transfected or transformed host cells can be used to make a protein of the present invention.

Control regions identified by the present invention and nucleic acid molecules comprising control regions identified by the present invention are useful, for example, as part of an expression vector to express a desired gene. Such expression vectors can be made by operably linking a control region of the present invention with a gene of interest using methods known in the art (Sambrook et al., supra, (1989)). Such vectors can be transfected or transduced into appropriate host cells using methods known in the (Sambrook et al., supra, (1989)). Within such cells, the control region can drive the expression or repress the expression of the gene of interest under a set of conditions, such as stresses, such as UV irradiation.

The function of the protein encoded by the protein coding region of SEQ ID NO: 16 is considered to be a nucleic acid molecule binding protein, such as a DNA binding protein based on homologies with known nucleic acid molecule binding proteins. For example, the sequence CDNFSAYG-WCPLGPQCPQSH (SEQ ID NO: 3) has an anchor blocks score of 1089 (88.6 percentile) matching with a zinc-finger motif based on BLOCKS search software (www.blocks.fh-cfc.org, Mar. 12, 1999). Also, the sequence IIDT-DEAAAEDKRRRRRRREKRKRALLNLPG (SEQ ID NO: 4) has an anchor blocks score of 1092 (90.1 percentile) matching with REV protein, an HIV anti-repression transcription activator, using BLOCKS search software. In addition, the sequence HRAGFDAFMTGYV (SEQ ID NO: 5) has an anchor blocks score of 1137 (98.1 percentile) matching with exonuclease, an ATP-dependent helicase, using BLOCKS search software. The function of proteins, polypeptides, peptides and fragments of active fragments thereof can be identified by determining amino acid sequence thereof, either by amino acid sequence reactions or by deducing the amino acid sequence from a nucleic acid sequence (see, Sambrook et al., supra, 1989). The function of a protein, peptide, polypeptide, or fragment or active fragment thereof can be inferred by comparing amino acid sequences or nucleic acid sequences encoding such amino acid sequences with appropriate databases, wherein substantial homology with an amino acid sequence or nucleic acid sequence of known function is predictive of the function of the nucleic acid molecule or protein identified by a method of the present invention.

The present invention also includes proteins identified by the present methods, such as the protein encoded by SEQ ID NO: 16, proteins having conservative amino acid substitutions thereof, and proteins having substantial identity thereto; and portions, fragments or active fragments of any of the foregoing or proteins comprising any of the foregoing.

The present invention also includes antibodies, either polyclonal or monoclonal, that specifically bind with a protein, portion thereof, fragment thereof or active fragment thereof of the present invention. Such antibodies can be made and screened for such specific binding using methods known in the art (Sambrook et al., supra, (1989); Harrow et al., Antibodies, A Laboratory Manual, Cold Spring Harbor Press, (1988)). Such antibodies are useful, for example, in immunoassays to detect the presence or amount of a protein, portion thereof, fragment thereof or active fragment thereof of the present invention. The antibodies can be linked to a detectable label, such as an enzyme such as horseradish peroxidase, radionucleotide such at $^{32}$P, fluorescent protein such as green fluorescent protein (GFP) or fluorophore such as rhodamine, using methods known in the art to detect the specific binding of the antibody.

III Nucleic Acid Molecule Arrays

In another aspect of the present invention, isolated nucleic acid molecule fragments, such as isolated DNA fragments or their cloned or amplified counterparts, or RNAs derived from the isolated nucleic acid molecule fragments, are labeled according to any technique as known or as may be developed in the art, such as with the cyanine dye dUTP analog Cy3 by polymerase chain reaction. Other labels, such as the fluorescent markers Cy5, fluorescein, rhodamine, or phycoerythrin, linked to nucleotides or nucleotide analogs, or radioisotopes such as $^{33}$P or $^{32}$P incorporated into nucleotides or nucleotide analogs, or biotin linked to nucleotides or nucleotide analogs, and other labeling techniques, such as nick translation, random priming, RNA synthesis, or reverse transcription of RNA derived from the DNA fragments, may be used (Yu, et al. NAR 22:3226–3232, Lockhart, et al., Nature Biotechnology 14:1675–1680; DeRisi, Nature Genetics 14:457–460, Chalifour, et al., Anal. Biochem 216: 299–304; Pietu, et al., Genome Research 6:4920–503). These labeled nucleic acid molecule fragments are added to hybridization reactions with nucleic acid molecule arrays, such as DNA arrays. These arrays may be synthesized or purchased and preferably contain sequences of expressed genes spotted on an ordered matrix made of glass, nitrocellulose, nylon, silicon, or other suitable material ((http:// cmgm.stanford.edu/pbrown/protocols; Scena, et al., Science 270:467–470; Pietu, et al., Genome Research 6:492–503; Chalifour, et al. Anal. Biochem, 216:299–304; Lockhart, et al., Nature Biotechnology 14:1675–1680; http://www-.clonetech.com; http://www.affymetric.com; http://www.incyte.com; Stratagene, 11011 North Torrey Pines, La Jolla, Calif. 92037). The sequences spotted on the array may be from any appropriate source. For example, databases such as Unigene and IMAG, (http://www.ncbi.nlm.nih.goiv/UniGene; http://wwwbio.llnl.gov/bbrp/image/image.html) provide catalogs of unique expressed sequence tags (ESTs) from human. Alternatively, the arrays may contain genes of known identity and may comprise genes encoding proteins of a particular type, for example, proteins that function in apoptosis. Hybridization reactions may be performed according to methods as known or developed in the future in the art (http://cmgm.stanford.edu/pbrown/protocols; Schene, et al. Science 270:467–470; Pietu, et al., Genome Research 6:492–503, Chalifour, et al., Anal. Biochem. 216: 399–304 and Lockhart et al. Nature Biotechnology 14:1675–1680) and positive hybridization signals are detected by machinery such as, in the case of fluorescently labeled probes, a confocal microscope that scans the array and detects the presence of labeled nucleic acid molecule (DeRisi, et al., Nature Genetics 14:457–460; Lockhart, et al., Nature Biotechnology 14:1675–1680). Scanning and detection systems using focused laser beams are available from Affymetrix (GeneArray™Scanner, Santa Clara, Calif., http://www.affymetrix.com), General Scanning (ScanArray™ Scanner, Menlo Park, Calif., http://www.genscan-.com), and Incyte (GemArray Scanner, Palo Alto, Calif., http://www.incyte.com), among other companies. If the probes are radiolabeled, the array may be subjected to autoradiography or phosphorimaging (Chalifour, et al. Anal. Biochem. 216:299–304, Pietu, et al., Genome Research 6:492–503). Other methods of detection may be used in accordance with the nucleic acid molecule labeling techniques that may be used in accordance with the nucleic acid molecule labeling techniques that may be used. The position of the labeled nucleic acid molecule may be localized on the array to identify the specific nucleic acid molecules, such as DNA molecules, on the array that have hybridized to the isolated nucleic acid molecule fragment (Lockhart, et al., Nature Biotechnology 14:1675–1680; DeRisi et al., Nature Genetics 14:457–460: Chalifour, et al. Anal. Biochem 216: 299–304 and Pietu, et al., Genome Research 6:492–503). Software is commercially available to facilitate the localization and determine the intensity of positive hybridization signals (the GeneChip Workstation Expression Data Mining Tool from Affymetrix, Santa Clara, Calif., the ScanArray™ Acquisition QukzantArray™ Tools from General Scanning, Menlo Park, Calif., and the GemTools™ LifeArray™ system from Incyte, Palo Alto, Calif.). Positively hybridizing nucleic acid molecules, such as DNA molecules, whether of known or unknown identity, are derived from genes presumptively regulated by the transcription factor.

EXAMPLES

Example 1

Identification of Control Elements and Genes Regulated by the Transcription Factor Egr-1

H4 cells subcloned from Fibrosarcoma HT1080 cells (ATCC NO: CCL-121) do not express detectable amounts of transcription factor EGR-1 (Huang et al., Cancer Res.55: 5054–5062 (1995)). Fibrosarcoma HT1080 sublime H4E9 (E9 cells) were prepared by transfection of H4 cells with expression vectors for mouse wild-type Egr-1 (pCMV-Egr-1) as described by Huang et al., Cancer Res. 55:5054–5062 (1995). These cells were maintained in DMEM supplemented with 10% fetal bovine serum and cultured in the presence of penicillin, streptomycin and 200 (micrograms/ ml of G-418. Cell numbers in culture were determined by direct cell counting following the general methods of Huang et al., Cancer Res. 55:5054–5062 (1995).

Separate cultures of H4 and E9 cells (approximately $5 \times 10^6$ to $1 \times 10^7$ cells) were irradiated with approximately 40 J/m$^2$ UV-C, a procedure that leads to new Egr-1 synthesis in cells with a normal Egr-1 gene. In E9 cells, this treatment leads to the hyperphosporylation of exogenous constitutive Egr-1, peaking at two hours. As controls, cultures of H4 and E9 cells that were not treated with UV-C were also subjected to the following procedures. The cells were contacted with 1% formaldehyde in 5 mM Tris, pH 8; 10 mM NaCl; 0.1 mM EGTA; 0.1 Mm EDTA, for about 2 hours following the general procedures of Orlando et al., Cell 75:1187–1198 (1993) to cross-link EGR-1 to its target DNA sequence. The cells were lysed in 4% SDS in 10 mM Tris, pH 8, 1 mM EDTA, and passage through a 20 gauge needle or by brief sonication. The cross-linked nucleic acids were separated using a urea gradient (about 5M to about 8M) using centrifugation at 30,000 rpm in a SW41 rotor (Beckman, Fullerton, Calif.) for about 16 hours. Fractions from the urea gradient were obtained, and fractions containing cross-linked nucleic acid molecules were identified in the pellets. Excess urea from these fractions was removed using dialysis.

Dialyzed fractions containing cross-linked nucleic acid molecules were treated with restriction enzyme Eco-RI (about 20 units overnight) at 37° C. to provide a mixture of cross-linked nucleic acid molecule fragments. The restriction enzyme digested preparation was precipitated using rabbit anti-Egr-1 antibodies using Protein-A Sepharose (Sigma Chemical Co., St. Louis, Mo.). The immunoprecipitates were collected by pelleting by centrifugation in a microcentrifuge.

Figure 2:
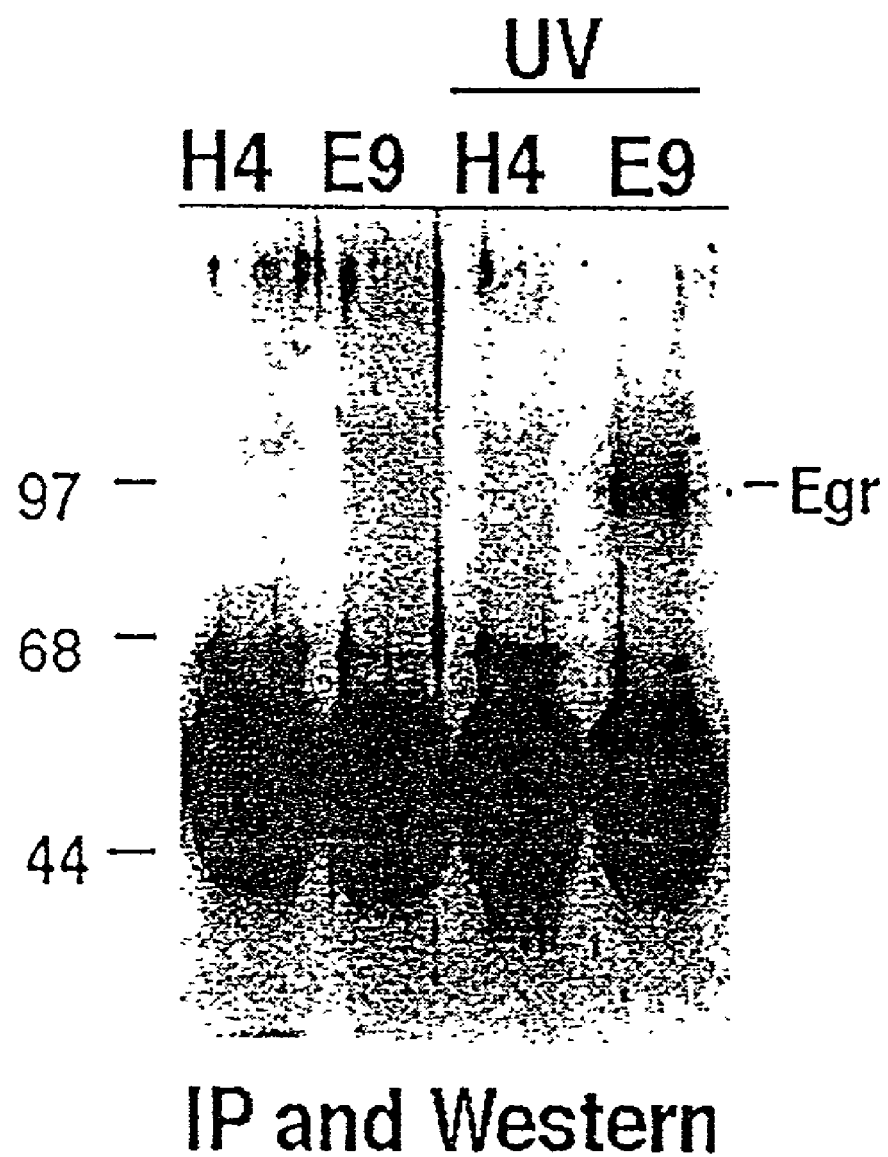
FIG. 2 depicts a Western Blot showing the recovery of Egr-1 from cross-linked nucleic acids.

To verify that Egr-1 was present in the immunoprecipitated fractions, samples of the immunoprecipitates were digested with DNase I (about 10 units at 37° C. for about 30 minutes) to release proteins bound to the nucleic acid molecule fragments. These preparations were separated using electrophoresis through a 10% SDS-PAGE gel. The protein in the gel was transferred to membranes and Western Blots were performed on the membranes using rabbit anti-Egr-1 antibodies, which were detected using anti-rabbit secondary antibodies conjugated to horseradish peroxidase and an appropriate detectable substrate (ECL) using horseradish peroxidase/hydrogen peroxide catalyzed oxidation of luminol. As shown in FIG. 2, Egr-1 protein was detected in samples derived from UV irradiated E9 cells, less in unirradiated H9 cells but not in irradiated H4 cells or unirradiated H4 cells.

Figure 3:
FIG. 3 depicts an ethidium bromide stained gel showing PCR products derived from nucleic acid molecules cross-linked to Egr-1.

For the remainder of the immunoprecipitates, the anti-EGR-1 antibodies and EGR-1 transcription factor were removed by treatment with proteinase K (0.25% SDS with 250 micrograms/ml of proteinase K, at 37° C. and 68° C. for about six hours. The resulting preparations of DNA fragments were ligated with linkers of the sequence 5'-AATTC-GAAGCTTGGATCCGAGCAG-3' (SEQ ID NO: 11) and 5'-CTGCTCGGATCCAAGCTTCG-3' (SEQ ID NO: 12) having Eco-RI ends, which ligate to the Eco RI-digested fragments. These fragments were then amplified in PCR using SEQ ID NO: 11 and SEQ ID NO: 12 oligonucleotide as the primers. The conditions used were 95° C. for 45 minutes, 55° C. for 30 minutes and 72° C. for 5 minutes. Samples of each of these reactions (H4, E9, H4/UV, and E9/UV) were electrophoresed through a 1% agarose gel and strained with ethidium bromide to detect nucleic acid molecules. As shown in FIG. 3, DNA was visibly amplified only from the E9 cells and from E9 cells irradiated with UV light. Immunoprecipitates from unirradiated H4 cells, and irradiated H4 cells, did not give rise to detectable levels of amplified DNA fragments.

The amplified DNA fragments were digested to completion with Eco-RI. The digested fragments were separated from linker-primer sequences by agarose gel electrophoresis and cloned into pBluescript plasmids by Eco-RI digestion of plasmids and subsequent ligation at 16° C. overnight. These plasmids were transformed to *E. coli* strain XL2B (Stratagene, San Diego, Calif.). Selected amplified DNA fragments were sequenced (SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24 and SEQ ID NO:25).

Figure 4:
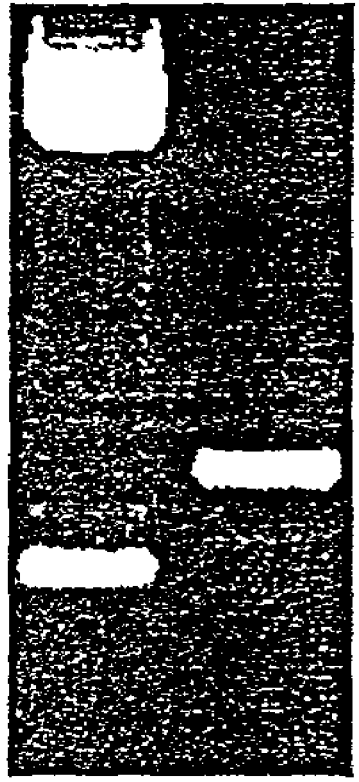
FIG. 4 depicts TGF-beta1 promoter region PCR products obtained using methods of the present invention.

To determine whether we could obtain promoter regions of genes regulated by Egr-1, an aliquot of the amplified isolated fragments in a PCR using primers from the promoter region of TGF-beta1 that spans −201 to +138 (339 base pairs) of human TGF-beta 1 promoter (5'-GGGCT-GAAGGGACCCCCCTC-3' (SEQ ID NO: 10) and 5"-TC-CTCGGCGACTCCTTCCTC-3' (SEQ ID NO: 1). A 339 base pair fragment was amplified from fragments isolated from nonirradiated E9 cells, which constitutively express EGR-1, but not from H4 cells (not shown), which are EGR-1 deficient (FIG. 4).

Figure 5:
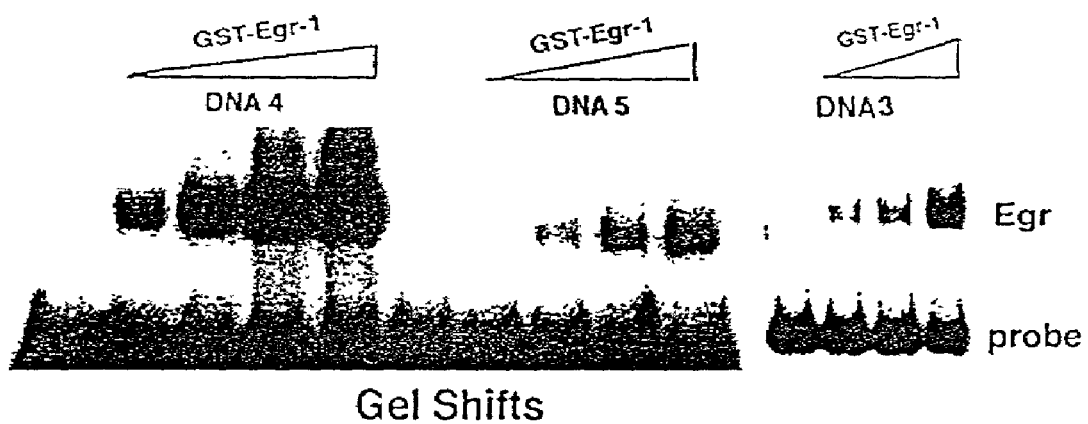
FIG. 5 depicts gel shift assays using nucleic acid molecules identified using a method of the present invention and recombinant Egr-1 protein.
Figure 6:
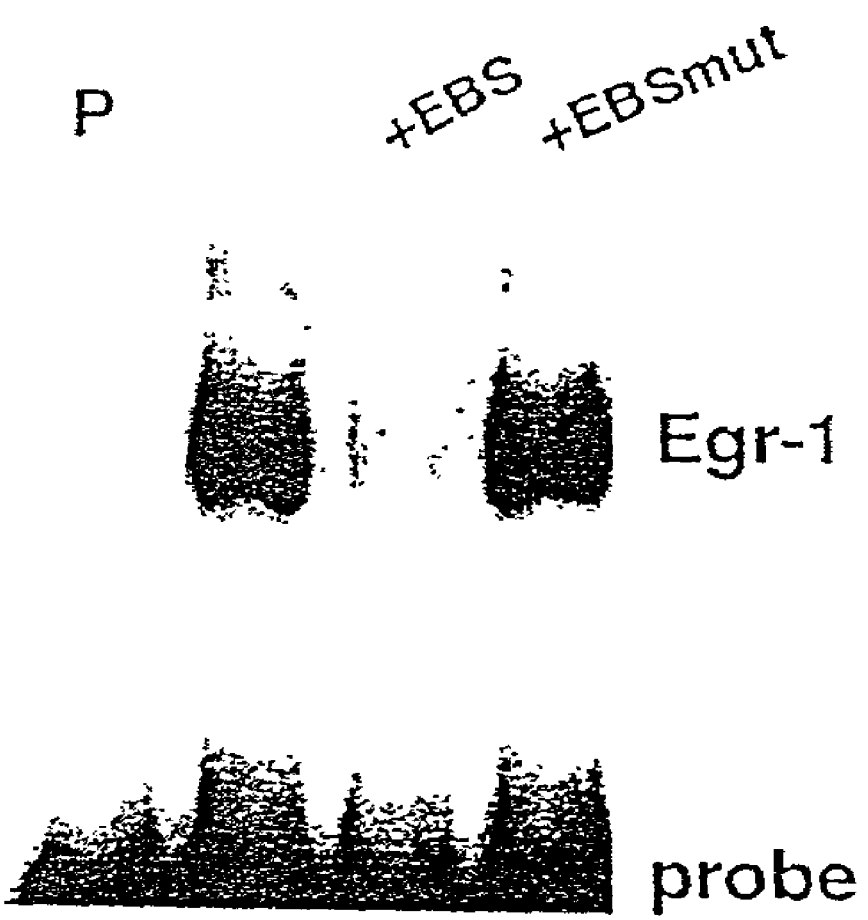
FIG. 6 depicts competitive gel shaft assays using recombinant Egr-1, Egr-binding domains and nucleic acid molecules identified by the methods of the present invention.

As a further test that the DNA fragments were isolated because they were bound by EGR-1, ten cloned inserts were isolated by digestion using Eco-RI and labeled with alpha-$^{32}$P-dATP by Klenow fill-in. The labeled nucleic acid molecules were mixed with bacterially synthesized EGR-1 protein, GST-Egr-1 between about 20 picoM and about 100 picoM. These mixtures were separated using electrophoresis under non-denaturing conditions in a 6% acrylamide gel. All ten cloned inserts exhibited gel shifts in the presence of GST-Egr-1, indicating that the nucleic acid molecule isolates bound to GST-Egr-1; gel shifts of three of these nucleic acid molecule isolates, DNA4, DNA5 and DNA3, are shown in FIG. 5. Nucleic acid molecule DNA4 from FIG. 5, labeled with alpha-$^{32}$P-dATP was subjected to competitive gel shift assays (FIG. 6). Briefly, labeled DNA4 (lane 1) was incubated with about 100 picoM egr-1 (lane 2) and then with excess unlabeled EBS (about 50X molar excess) Wild-type Egr-1 binding site, 5'-GATCACTCGCGGGGGCGAGGAT-GAGCGCCCCCGCTCCTCTTAG-3' (SEQ ID NO:13) (lane 3) or mutant EBS (EBSmut) that does not bind with Egr-1,5'-GATCACTCACATTTACAAGGATGAGTG-TAAATGTTCCTCTAG-3' (SEQ ID NO:14) (lane 4). As shown in FIG. 6, EBS, but not EBSmut, competed with the binding of DNA4 with Egr-1.

Figure 7:
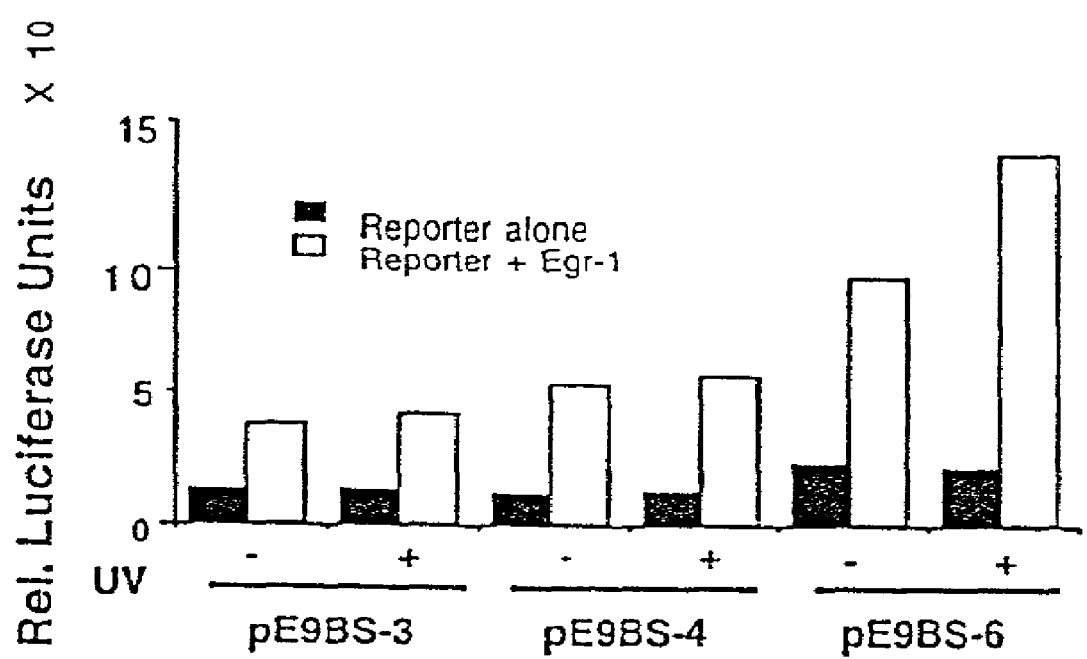
FIG. 7 depicts the functionality of the nucleic acids of the present invention as modulators of gene expression using a reporter gene in vivo.

Three of the DNA fragments of the present invention were functionally linked to a reporter gene to determine the functionality of the isolated nucleic acid molecule sequence. Sequences E9BS-3, E9BS-4 and E9BS-6 were functionally linked to a luciferase gene having a minimal (fos56-promoter by cloning into plasmid pGL3-Basic (Promega, Madison, Wis.) to form pE9BS-3, pE9BS-4 and pE9BS-6. This plasmid was transfected in H4 cells, which does not express EGR-1, with and without cotransfection of EGR-1 expression plasmid pCMV-Egr-1. The transfected cell lines were then either untreated or irradiated with UV-C (40 J/m$^2$) and the amount of luciferase in the untreated or treated cells measured. As shown in FIG. 7, all of the fragments tested shown EGR-1 induced stimulation of expression of the reporter gene. In addition, E9BS-6 showed increased expression of the reporter gene after irradiation.

Example 2

Isolation of Expressed Genes by PCR Using a cDNA Library

Figure 8:
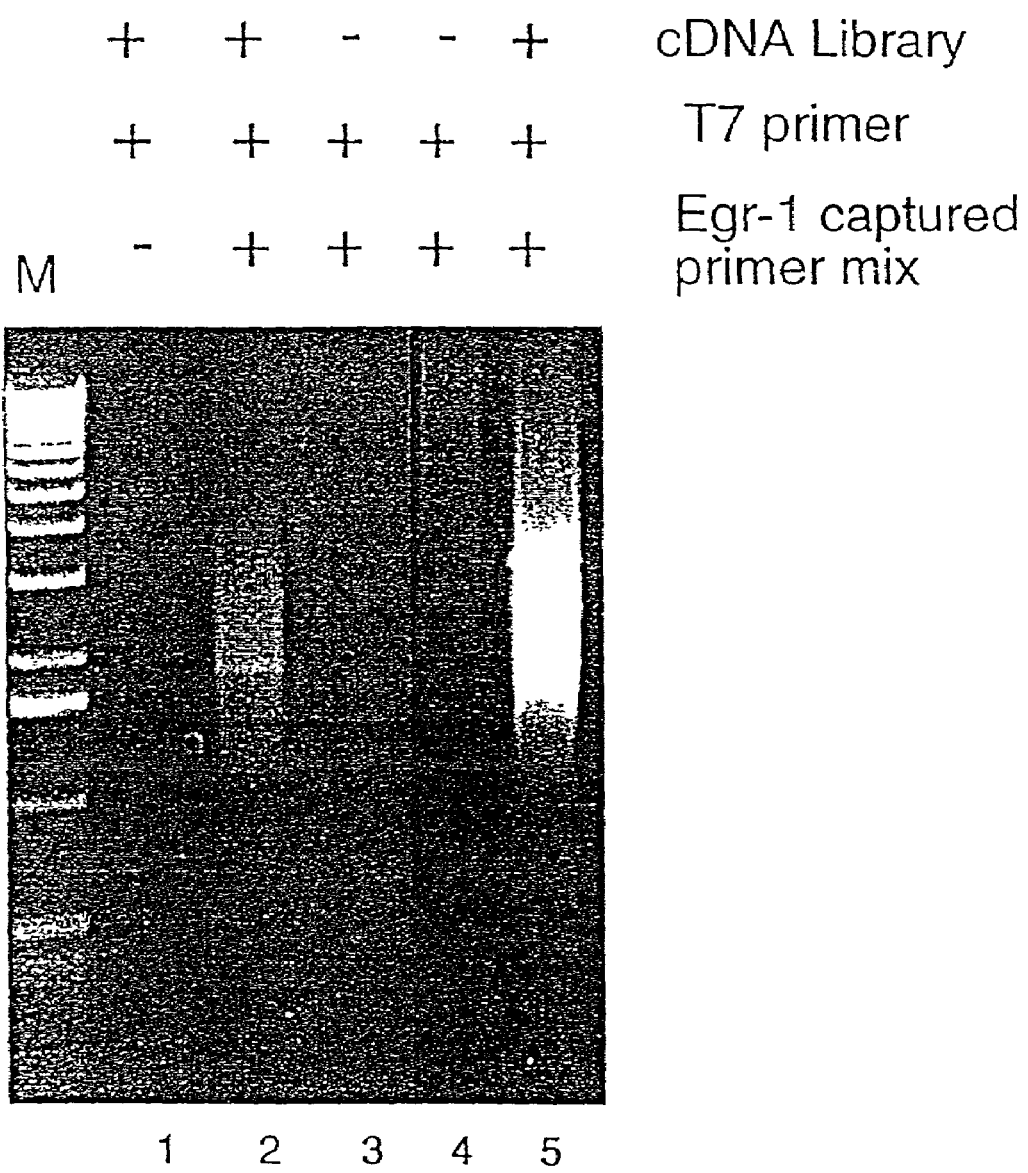
FIG. 8 depicts PCR amplification products from two independent amplifications (lane 2 and lane 5) derived from a mixture of a cDNA library and a 5' PCR primer derived from DNA cross-linked to Egr-1 in a living cell, and a 3' primer derived from a library vector sequences.

Bacteria containing the plasmids containing the isolated fragments as inserts described in Example 1 were grown as a bulk, mixed culture and plasmid DNA was isolated using Qiagen maxi-prep columns generally following the manufacturers instructions. The isolated plasmid DMA was digested with EcoRI (about 10 units for about 4 hours) to release DNA inserts. The digest was electrophoresed on a 1% agarose gel, and gel sections containing digested inserts was excised. The DNA inserts were isolated from the gel using a Qiagen maxi-prep column generally following the manufacturers instructions. The DNA inserts, a mixture of man different clones of many different sequences, was mixed with DNA isolated by excision from a lambda-gt11 library. The library was made from RNA isolated from the NT2 human carcinoma cell line, (ATCC NO: CRL-1973) which is known to express EGR-1, and was purchased from Stratagene. The T7 vector primer (5'-TAATACGACTCAC-TATAGGGAGA-3' (SEQ ID NO: 2) was added to the mixture to serve as a 3' primer in the amplification reaction. PCR was performed under the following conditions: 95° C. for 45 minutes, 50° C. for 30 minutes, 72° C. for 5 minutes for thirty cycles. These PCR conditions were optimized by varying the amount of isolated DNA insert used in the PCR reactions so that when products of the PCR reactions were electrophoresed on agarose gels and stained with ethidium bromide, bands were visible in the PCR which contained the cDNA library and the isolated fragment inserts, but not in control reactions which lacked either the cDNA library DNA or the isolated DNA inserts (FIG. 8).

The products of the PCR were separated on a 1% agarose gel. Seven ethidium bromide stained bands were excised from the gel and the DNA was isolated and clone into a TA plasmid vector pCR 3.1 from Invitrogen. One of the seven clones obtained was sequenced. The 5' end of the clone was found to contain sequences approximating the Egr-1 binding site. Sequence analysis also revealed a putative TATA site preceding an open reading frame (702 base pairs) (FIG. 11). Another clone that was obtained was also sequenced similarly to the first clone. The cDNA sequence (SEQ ID NO: 27) and protein sequence (SEQ ID NO: 26) of this clone are shown in FIG. 14.

Figure 9:
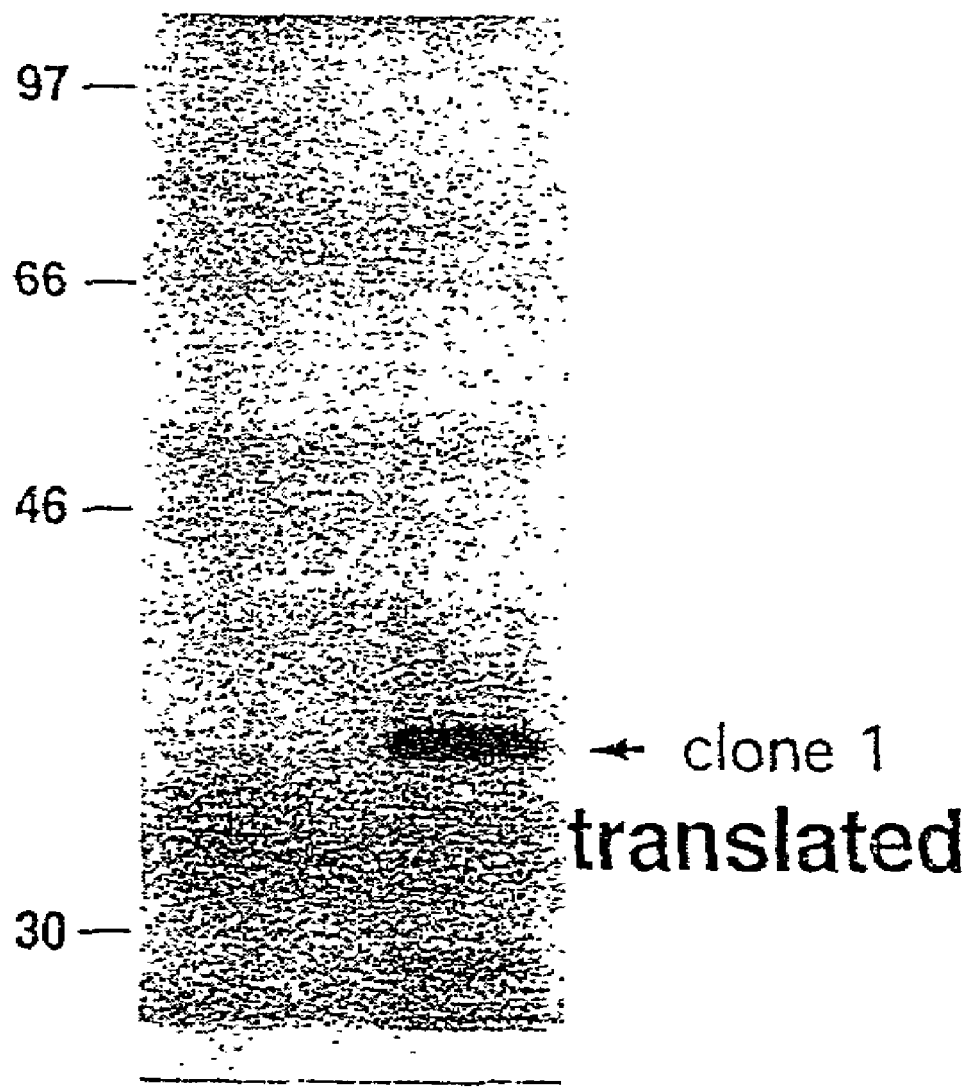
FIG. 9 depicts in vitro transcription and translation of a DNA sequence obtained using the methods of the present invention to obtain a 37 kDa protein (SEQ ID NO: 16).

Clone 1 (SEQ ID NO: 15) was used as a template in an in vitro transcription and translation reaction to produce a protein determined to be approximately 37 kDa by comparison with standard molecular mass markers when subjected to electrophoresis through 10% SDS-PAGE. The in vitro transcription and translation reaction was performed using the TnT-coupled reticulocyte lysate system generally according to the manufacturer instructions (Promega, Madison., WI). For the reaction, 1 microgram of clone 1 template DNA or control empty vector DNA was used in the presence of 10 U of T7 RNA polymerase (Promega, Madison, Wis.), and 40 microCi of $^{35}$S-Methionine (NEN, Boston, Mass.). Products were analyzed by 10% SDS-PAGE followed by autoradiography with Kodak XR5 X-ray film. FIG. 9 shows that the control empty vector produced no protein, while clone 1 (SEQ ID NO: 15) DNA produced a polypeptide of approximately 37 kDa.

Figure 10:
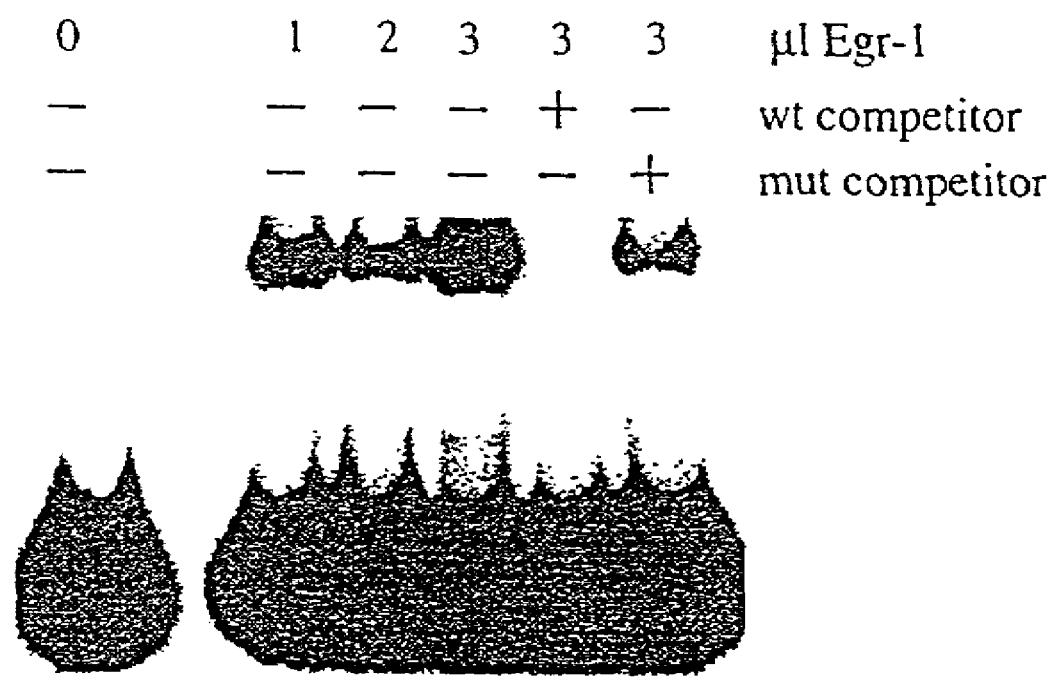
FIG. 10 depicts a gel shift assay for binding of Egr-1 to the 5' region of a nucleic acid molecule isolated using the methods of the present invention.

A gel shift assay was performed using a probe derived from the 5' region of clone 1 (FIG. 10). The probe was generated by PCR using specific primers designed to amplify the region encompassing nucleotides 507 to 700 of SEQ ID NO: 15 generating a probe of 193 base pairs. The sequence of this probe is indicated in FIG. 11 in bold type. The 5' and 3' primers used to generate the probe were 5'-TACCATAAGGGCAATGACAA-3' (SEQ ID NO: 6) and 5'-CATCTCACACAGGTCAGCGGT-3' (SEQ ID NO: 7) respectively. The PCR product was radiolabelled using 10U of T4 kinase (Gibco, Life Technologies, Gaithersburg, Md.), in the presence of 50 microCi of $^{32}$P-ATP. For the gel shift assay, 10,000 to 20,000 cpm of probe was mixed with 1 microgram of poly(dI-dC) (Pharmacia, Peapak, N.J.), as non-specific competitor DNA, and 20 to 60 pmol of bacterially produced recombinant Egr-1, in a buffer consisting of 10 mM HEPES, pH 7.9/10% (v/v) glycerol/1 mM DTT/50 mM KCl/2.5 mM mgCl$_2$. The tubes were incubated at room temperature for 15 minutes, and then either consensus Egr-1 binding site or mutated binding site oligonucleotides as previously described were added to the appropriate tubes at a 50 fold molar excess to the probe. The tubes were incubated for a further 15 minutes at room temperature, and were then subjected to non-denaturing gel electrophoresis through a 6% polyacrylamide gel containing 10 mM TRIS, pH 8.7/60 mM EDTA. Following electrophoresis, the gel was dried and subjected to autoradiography with Kodak XR5 X-ray film.

Recombinant Egr-1 was prepared by cloning the coding sequence of Egr-1 into the pGEX-2T vector (Pharmacia Peapak, N.J.) in frame. This cloning generated a GST-Egr-1 fusion protein, which was expressed in and purified from XL2B cells using glutathione-agarose beads generally according to the manufacturers instructions (Pharmacia, Peapak, N.J.). For this in frame cloning, Egr-1 was generated by PCR using specific primers designed to amplify from amino acids 2 to 533 of mouse Egr-1. The template for PCR was mouse Egr-1 cloned into the plasmid vector pcDNA3 (Invitrogen), and the primers used were 5'-CGCG-GATCCGCAGCGGCCAAGGCC-3' (SEQ ID NO: 8) and 5'-CCGGAATTCGCAAATTTCAATTGT-3' (SEQ ID NO:9) containing BamHI and EcoRI sites respectively, which were digested post-PCR to allow in frame cloning into BamHI and EcoRI digested PGEX-2T vector. The sequence of the competitor oligonucleotides used in the shift assay were as used in FIG. 6. FIG. 10 shows that recombinant Egr-1 is able to specifically bind to this region of clone 1. A potential Egr-1 binding site within this region is indicated in FIG. 11 in bold italics.

Figure 12:
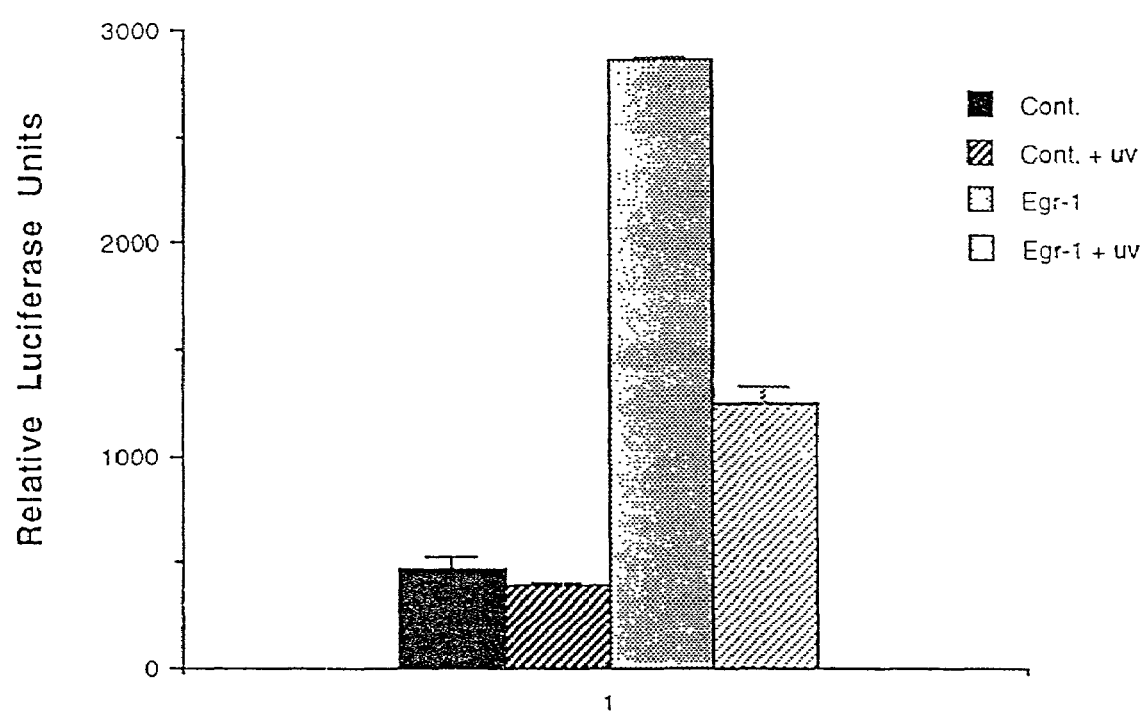
FIG. 12 depicts a luciferase assay using the 5' non-coding region of Clone 1 upstream of a luciferase reporter gene assay in vivo.
Figure 13:
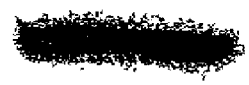
FIG. 13 depicts in vitro transcription and translation of the TOE1 DNA sequence obtained using the methods of the present invention to obtain a 60 kDa protein (Lane 2, SEQ ID NO: 26).

To generate a clone 1 reporter construct, the 5' region of clone 1 containing nucleotides 1 to 922 of SEQ ID NO: 15 was cloned into the pGL3-Basic Luciferase reporter vector (Promega Madison, Wis.) (FIG. 12). A clone 1 reporter construct was generated by digesting the original clone 1, inserted into pCR 3.1 TA vector, with KpnI and PvuII. The 922 base pair digestion product consisting of the 5' region of clone 1 was then purified by 1% agarose gel electrophoresis, and then ligated into the pGL3-Basic vector which had been digested with KpnI and SmaI. The transcriptional effects of Egr-1 on this reporter construct were determined by transient transfection assays in 293T cells. For these assays, 0.5 microgram of the reporter construct (pGL3-luciferase reporter with the 5' region of clone 1) was transfected together with 3 microgram of an Egr-1 expression construct, or the same amount of the corresponding empty vector, and 0.2 microgram of pCMV-beta-gal vector by liposome mediated transfection with the Lipofectamine reagent according to the manufacturers instructions (Gibco, Life Technologies Gaithersburg, Md.). Twenty-four hours after transfection, the same dishes of cells were irradiated with 40 J/m$^2$ of UV-C radiation using a Stratalinker (Stratagene, San Diego, Calif.). Four hours after irradiation the cells were harvested and lysed in a buffer consisting of 100 mM KPO4, pH 7.8/0.2% (w/v) Triton X-100/1 mM DTT. For each sample, the beta-galactosidase (GAL) activity was measured by incubating a fraction of the cell extract with 400 micrograms of ONPG (O-nitrophenyl-D-galactopyranoside) at 37° C. for 10 to 30 minutes. The resulting reaction was measured spectrophotometrically at 420 nm. The spectrophotometric readings were used to equalize for transfection efficiencies for the Luciferase reporter assays. For the Luciferase assays, the corrected amount of cell extract was mixed with 0.07 mM luciferin substrate (D-Luciferin, potassium salt, Analytical Luminescence Laboratory), in the presence of 0.01 M ATP. Luciferase activity was measured in a 96 well microtiter plate in an EG&G Berthold microL umat LB96P Luminometer. FIG. 12 shows that, when transfected in 293T cells, Egr-1 transactivates the reporter construct, while UV-activated Egr-1 represses transactivation activity. These results demonstrate that Egr-1 up-regulates cone 1 gene, but UV-irradiation presumably leads to the formation of phosphorylated Egr-1 which then represses transcription of clone 1 gene. This is the first demonstration that Egr-1 modification alters its trans-activating function.

All publications, including patent documents and scientific articles, referred to in this application are incorporated by reference in their entirety for all purposes to the same extent as if each individual publication were individually incorporated by reference.

All heading are for the convenience of the reader and should not be used to limit the meaning of the text that follows the heading, unless so specified.

We claim:

1. A method for identifying one or more cDNA molecules that correspond to one or more genes regulated by a transcription factor, comprising:
   a) cross-linking at least one transcription factor to at least one nucleic acid molecule in at least one cell or at least one nucleus, forming one or more transcription factor-nucleic acid molecule complexes;
   b) fragmenting said at least one nucleic acid molecule to form one or more transcription factor-nucleic acid molecule fragment complexes;
   c) isolating one or more nucleic acid molecule fragments from said one or more transcription factor-nucleic acid molecule fragment complexes to form one or more isolated nucleic acid molecule fragments;
   d) combining said one or more isolated nucleic acid molecule fragments with either:
      1) a cDNA library, or
      2) cDNA obtained by reverse transcription of a population of RNA molecules, to form a mixture comprising isolated nucleic acid molecule fragment/cDNA complexes; and
   e) amplifying one or more cDNAs that binds with said one or more isolated nucleic acid molecule fragments using said one or more nucleic acid molecule fragments as primers to obtain one or more isolated cDNA molecules, said one or more isolated cDNA molecules comprising at least a portion of a gene operably linked to or in close proximity to a nucleic acid sequence that binds with at least one transcription factor; and f) identifying said one or more cDNAs by either:
   1) sequencing said one or more cDNAs and comparing said sequence to the sequences of DNA molecules of known sequence, or
   2) hybridizing said one or more cDNAs to one or more nucleic acid molecules corresponding to known genes or nucleic acid sequences.

2. The method of claim 1, wherein said amplifying comprises cloning said one or more isolated cDNA molecules in at least one vector.

3. The method of claim 1, wherein said at least one nucleic acid molecule comprises genomic DNA.

4. The method of claim 1, wherein said transcription factor is selected from the group consisting of leucine zipper factors, helix-loop-helix factors, helix-loop-helix/leucine zipper factors, NF-1 factors, RF-X factors, bHSH factors, Cys4 zinc finger of nuclear receptor factors, diverse Cys4 zinc finger factors, Cys2His2 zinc finger factors, Cys6 cysteine-zinc cluster factors, Homeo domain factors, paired box factors, fork head/winged helix factors, heat shock factors, tryptophane cluster factors, TEA domain factors, RHR factors, p53 factors, MADS box factors, beta-barrel alpha-helix factors, TATA-binding factors, HMG factors, heteromeric CCAAT factors, Grainyhead factors, cold-shock domain factors, Runt factors, copper fist factors, HMGI(Y) factors, STAT factors and pocket domain factors.

5. The method of claim 1, wherein said transcription factor is Egr-1.

6. The method of claim 1, wherein at least one cell or at least one nucleus is at least one cell.

7. The method of claim 6, wherein at least one cell is at least one living cell.

8. The method of claim 7, wherein said at least one living cell is irradiated prior to said cross-linking.

9. The method of claim 1, wherein said cross-linking is performed using formaldehyde.

10. A method according to claim 1 wherein said hybridizing said one or more cDNAs to one or more nucleic acid molecules corresponding to known genes or nucleic acid sequences is to an array of said nucleic acid molecules corresponding to known genes or nucleic acid sequences.

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Homo sapiens

<400> SEQUENCE: 1
tcctcggcga ctccttcctc                                               20

<210> SEQ ID NO 2
<211> LENGTH: 23
<212> TYPE: DNA
<213> ORGANISM: Homo sapiens

<400> SEQUENCE: 2
taatacgact cactataggg aga                                           23

<210> SEQ ID NO 3
<211> LENGTH: 20
<212> TYPE: PRT
<213> ORGANISM: Homo sapiens

<400> SEQUENCE: 3

Cys Asp Asn Phe Ser Ala Tyr Gly Trp Cys Pro Leu Gly Pro Gln Cys
1               5                   10                  15

Pro Gln Ser His
            20

<210> SEQ ID NO 4
<211> LENGTH: 31
<212> TYPE: PRT
<213> ORGANISM: Homo sapiens

<400> SEQUENCE: 4

Ile Ile Asp Thr Asp Glu Ala Ala Ala Glu Asp Lys Arg Arg Arg Arg
1               5                   10                  15

Arg Arg Arg Glu Lys Arg Lys Arg Ala Leu Leu Asn Leu Pro Gly
            20                  25                  30

<210> SEQ ID NO 5
<211> LENGTH: 13
<212> TYPE: PRT
<213> ORGANISM: Homo sapiens

<400> SEQUENCE: 5

His Arg Ala Gly Phe Asp Ala Phe Met Thr Gly Tyr Val
1               5                   10

<210> SEQ ID NO 6
<211> LENGTH: 20
<212> TYPE: DNA
<213> ORGANISM: Homo sapiens

```
<400> SEQUENCE: 6
taccataagg gcaatgacaa                                              20

<210> SEQ ID NO 7
<211> LENGTH: 21
<212> TYPE: DNA
<213> ORGANISM: Homo sapiens

<400> SEQUENCE: 7
catctcacac aggtcagcgg t                                            21

<210> SEQ ID NO 8
<211> LENGTH: 24
<212> TYPE: DNA
<213> ORGANISM: Homo sapiens

<400> SEQUENCE: 8
cgcggatccg cagcggccaa ggcc                                         24

<210> SEQ ID NO 9
<211> LENGTH: 23
<212> TYPE: DNA
<213> ORGANISM: Homo sapiens

<400> SEQUENCE: 9
ccggaattcg caaatttcaa ttg                                          23

<210> SEQ ID NO 10
<211> LENGTH: 20
<212> TYPE: DNA
<213> ORGANISM: Homo sapiens

<400> SEQUENCE: 10
gggctgaagg gacccccctc                                              20

<210> SEQ ID NO 11
<211> LENGTH: 24
<212> TYPE: DNA
<213> ORGANISM: Homo sapiens

<400> SEQUENCE: 11
aattcgaagc ttggatccga gcag                                         24

<210> SEQ ID NO 12
<211> LENGTH: 20
<212> TYPE: DNA
<213> ORGANISM: Homo sapiens

<400> SEQUENCE: 12
ctgctcggat ccaagcttcg                                              20

<210> SEQ ID NO 13
<211> LENGTH: 43
<212> TYPE: DNA
<213> ORGANISM: Homo sapiens

<400> SEQUENCE: 13
gatcactcgc gggggcgagg atgagcgccc ccgctcctct tag                    43

<210> SEQ ID NO 14
<211> LENGTH: 42
<212> TYPE: DNA
```

<213> ORGANISM: Homo sapiens

<400> SEQUENCE: 14

```
gatcactcac atttacaagg atgagtgtaa atgttcctct ag                    42
```

<210> SEQ ID NO 15
<211> LENGTH: 2007
<212> TYPE: DNA
<213> ORGANISM: Homo sapiens

<400> SEQUENCE: 15

```
taatacgact cactataggg agacgagcgg tgtcatggcc gccgacagtg acgatggcgc    60
agtttcagct cccgcagctt ccgacggtgg tgtcagcaaa agcacaacat ctggggagga   120
gctagtagtc caggttcccg tagtggatgt gcaaagcaac aacttcaagg agatgtggcc   180
atccctcctg ctagccataa agacagctaa tttcgttggc tgtggacacg agctgagtg    240
ggcttgggga caagaagagt ttgctgaacc agtgcattga ggaacgttac aaggccgtgt   300
gtcatgctgc caggacccgt tctatccttt ccctgggcct cgcctgcttc aagcggcagc   360
cagacaaggg tgaacattcc tatctggctc aagtgttcaa tctcactctg ctgtgcatgg   420
aggagtatgt catagaacca aagtctgtgc agttcctgat acagcatggc ttcaacttca   480
accagcagta tgcccaaggc atcccctacc ataagggcaa tgacaagggt gatgagagcc   540
agagccagtc agtacggacc ctattcctgg agctaatccg aagcccgccg gcccctgttg   600
ctacacaatg gccttataga cttggtgttc ctgtaccaaa acttctatgc cacctcccct   660
gagagtctgg gaaccttcac cgctgacctg tgtgagatgt tcccagcagg catttatgac   720
accaaatatg ctgctgagtt tcatgcccgt ttcgtggcct cctacttaga atatgccttc   780
cggaaatgtg ttttaggtgc tgaggattca gcagtgaaca aaacagacca caaaaccctg   840
ctcttatgga gcttatatgc tagtggacca ttaccctctt cgcgtgttgc agtgaacggg   900
aaaatgggaa gcagcgggca gctggcagcc cacaccttac cctggagttc tgcaactatc   960
cttccagcat gagggaccat attgattacc gctgctgcct gccccagca acccaccgtc  1020
ctcatcccac cagcatctgt gacaacttct cggcttatgg ctggtgcccc ctgggaccac  1080
agtgtcctca gtctcacgat attgacccta tcattgacac tgatgaggct gcggcagagg  1140
acaagcggcg acggcgacga cgtagggaaa acggaagag ggctttattg aacctaccgg  1200
ggacacagac ctctggggaa gctaaggatg gtcctcccaa gaagcaggtc tgtgggggata  1260
gcatcaagcc tgaagaaacc gagcaggagg tggctgccga tgaaactagg aacctgcctc  1320
actccaagca aggcaacaaa aatgactag agatggggat taaggcagca aggcctgaaa  1380
tagctgatag agctacctca gaagtgccag ggagccaagc cagtcctaac ccagtgcctg  1440
ggggtggatt gcaccgggct ggttttgatg cctttatgac aggttatgtg atggcctatg  1500
tggaagtgag ccagggaccg caaccctgca gctctgacc ctggctccct gaatgccaca  1560
ataaggtata tttgagtggc aaagctgtac ccctcacagt ggccaagagc cagttctctc  1620
gttcctccaa agcccacaat cagaagatga agctcacttg gggcagtagc tgatgcaact  1680
tccaccttgc tctcaggtgg aacagaggta ttttgggtct ctctagcctg aaatgtcatc  1740
ctcaactgct actgagtttg ggggaggggg aatgtcttga cagacatcac tgcattgccc  1800
tggaccgcct cctttatccc agtgtttgag gtacaagtaa aaggctgac cagcacctgt  1860
aacactgact ttattttaa gtctgaaaat gtcttgggaa gtttacaa aaaaaaaaat  1920
caacagaagc aagttatgaa aaaaaaaaa aaaaaaaac tcgaggggg gcccggtacc  1980
```
caattctccc tatagtgagt cgtatta                                                                    2007

<210> SEQ ID NO 16
<211> LENGTH: 234
<212> TYPE: PRT
<213> ORGANISM: Homo sapiens

<400> SEQUENCE: 16

Met Arg Asp His Ile Asp Tyr Arg Cys Cys Leu Pro Pro Ala Thr His
1               5                   10                  15

Arg Pro His Pro Thr Ser Ile Cys Asp Asn Phe Ser Ala Tyr Gly Trp
            20                  25                  30

Cys Pro Leu Gly Pro Gln Cys Pro Gln Ser His Asp Ile Asp Pro Ile
        35                  40                  45

Ile Asp Thr Asp Glu Ala Ala Ala Glu Asp Lys Arg Arg Arg Arg Arg
    50                  55                  60

Arg Arg Glu Lys Arg Lys Arg Ala Leu Leu Asn Leu Pro Gly Thr Gln
65                  70                  75                  80

Thr Ser Gly Glu Ala Lys Asp Gly Pro Pro Lys Lys Gln Val Cys Gly
                85                  90                  95

Asp Ser Ile Lys Pro Glu Glu Thr Glu Gln Glu Val Ala Ala Asp Glu
            100                 105                 110

Thr Arg Asn Leu Pro His Ser Lys Gln Gly Asn Lys Asn Asp Leu Glu
        115                 120                 125

Met Gly Ile Lys Ala Ala Arg Pro Glu Ile Ala Asp Arg Ala Thr Ser
    130                 135                 140

Glu Val Pro Gly Ser Gln Ala Ser Pro Asn Pro Val Pro Gly Gly Gly
145                 150                 155                 160

Leu His Arg Ala Gly Phe Asp Ala Phe Met Thr Gly Tyr Val Met Ala
                165                 170                 175

Tyr Val Glu Val Ser Gln Gly Pro Gln Pro Cys Ser Ser Gly Pro Trp
            180                 185                 190

Leu Pro Glu Cys His Asn Lys Val Tyr Leu Ser Gly Lys Ala Val Pro
        195                 200                 205

Leu Thr Val Ala Lys Ser Gln Phe Ser Arg Ser Ser Lys Ala His Asn
    210                 215                 220

Gln Lys Met Lys Leu Thr Trp Gly Ser Ser
225                 230

<210> SEQ ID NO 17
<211> LENGTH: 724
<212> TYPE: DNA
<213> ORGANISM: Homo sapiens
<220> FEATURE:
<221> NAME/KEY: misc_feature
<222> LOCATION: (2)..(710)
<223> OTHER INFORMATION: n= A, T, G, or C

<400> SEQUENCE: 17
gnngggngnn gnnnnngggg gaacttntat cggtgcctac tcacngaaaa ggctgaagag      60
tctcccatgt ctacttcttt ctacacagac acagcaacca tccgatttct caatcttttc    120
cccacctttc ccccttttct attccacaaa accgccattg tcatcatggg ccgttctcaa    180
tgagctgttg ggtgagatat tagaattcta ctcacagaac gaaatgaaaa gtctcccatg    240
tctacttctt ctacacaaga cacagcaaca tccgatttct caatcctttc ccaactttc     300 cccctttct antccacaan accgccattg tcatcatggg ncgttctcaa tgagctgttg     360

```
ggtgagatat tagaattctg ggctgggaat gagttcagcc tggtggaatg tgaacctgca      420
ncagtttggc atgaacgggc aaatgctgtg tanccteegg aaaggagegc ttcctggaag      480 ctggcgcctg actttgtggg ngacatcctc cggaaaang gttcactant tctaaagcgg      540
gcggcaacgc ggtggggctc caattcgccc taaantgngt ccgtattaca attcacnggg      600
cggccgtttt anaagtcctg nncggggaaa accnggggta nccaacttta tcnccctggn      660
ngaaancccc ccttncncaa cnggggtnan aaccnannng ggccncccnn tttgcccctc      720
ccaa                                                                   724
```

<210> SEQ ID NO 18
<211> LENGTH: 618
<212> TYPE: DNA
<213> ORGANISM: Homo sapiens
<220> FEATURE:
<221> NAME/KEY: misc_feature
<223> OTHER INFORMATION: n = A, T, C, or G
<220> FEATURE:
<221> NAME/KEY: misc_feature
<222> LOCATION: (437)..(618)
<223> OTHER INFORMATION: n = A, T, C, or G

<400> SEQUENCE: 18

```
agaagcttga attcgagcag agaagcttga attcgagcag aattggccca attttgcctt       60
ataccacttt ccaataccct cacttggagt gacttacact gtggttaatt gcagttacaa     120
tgaagagatt aacatgggaa tgtcataata attgaatcta agaagacat aatttcaaaa      180 taagagcttg agtaataata ccattgtgta acaatctgat ttccatccct cttatttttc     240
ctatattatg cagtttagtt ctttactatc atgtgtttca tgtttgttcg gttttaccaa     300
cacatcatta gtaaattgaa tgtaaggctt ctcatttctt ttgtatccta catctaaaag     360
attttagtcc ttagaatcct cttgaaatgt tctccattta aaatggagaa atagttcatg     420
ctctctcatc taagtangag ctaaaatcta aaaattaat aaataaaata gtccatcctc      480
taataataat aatgaatact gaatttgtta antaataatt aattttgag aaggggttc       540 actaatgcgt ccaagctgga gtgcaatggc gtgatcacta anttctaaan cggcgccaac    600
gcggtggagc tccaantn                                                  618
```

<210> SEQ ID NO 19
<211> LENGTH: 716
<212> TYPE: DNA
<213> ORGANISM: Homo sapiens
<220> FEATURE:
<221> NAME/KEY: misc_feature
<223> OTHER INFORMATION: n = A, T, C, or G
<220> FEATURE:
<221> NAME/KEY: misc_feature
<222> LOCATION: (3)..(711)
<223> OTHER INFORMATION: n = A, T, C, or G

<400> SEQUENCE: 19

```
ggngtgggng nnngggggg ggnntttnng gnncggntnt tctnaagtnt ccngggcctc       60
atnaaacagc gggccgagaa cgggncaana tgacaatggn ggttttgtgg aatagaaaag    120
ggggaaaggt gggaaatga ttgagaaatc ggatggttgc tgtgtctgtg tagaaagaag    180
tagacatggg agacttttca ttttgttctg tgagtagaat tctgggctgg gaatgagttc    240
agcctggtga atgtgaacct gcaccagttt ggcatgaacg gncagatgct gtgtaacctc    300
ggcaaggagc gcttcctgga gctggcgcct gactttgtgg gcgacatcct ctggnacagg    360
```

```
ntccactagt tctagagcgg gcgccaccgc ggtggngctc caattcgccc tanagtgngt      420
cgtnttacaa ttcactggcc gtcgttttac aacgtcgtga ctgggaaaac cctggngtta      480
cccaacttaa tcgccttgca gcanatcccc ctttcgncag ctgggngtnnt ancgangagg      540 nccgcaccgn ttgcccntcc caanaagttg cgcagcctgn atgggantg ggancgncct       600 gtnncgggng cantaagcgc ggnggtgtg gtggntangc ncancgtgnn cgnnnnannt        660
gnnagngcct tangccngnn ccttcgnttc tcccttcctt cnngnnangt ngcggg           716

<210> SEQ ID NO 20
<211> LENGTH: 619
<212> TYPE: DNA
<213> ORGANISM: Homo sapiens
<220> FEATURE:
<221> NAME/KEY: misc_feature
<222> LOCATION: (326)..(609)
<223> OTHER INFORMATION: n = A, T, C, or G

<400> SEQUENCE: 20
agaagcttga attcgagcag agaagcttga attcgagcag aattggccca attttgcctt      60
ataccacttt ccaatacctt cacttggagt gacttacact gtggttaatt gcagttacaa     120
tgaagagatt aacatgggaa tgtcataata attgaatcta agaagacat aatttcaaaa      180 taagagcttg agtaataata ccattgtgta acaatctgat ttccatccct cttatttttc     240
ctatattatg cagtttaagt tctttactat catgtgtttc atgtttgttc ggttttacca     300
acacatcatt agtaaattga atgtanggct tctcatttct tttgtatcct acatctaaaa     360
gattttagtc tttagaatcc tcttgaaatg ttctccattt aaaatggaga aatagttcat     420
gctctctcat ctaantanga gctaaaatct aaaaaataaa taataaaat antccatcct     480 ctaataataa taatgaatac tgaanttgta aataataatt aattttttgag aatggggttc    540 actaatgtcg tccaanctgg agtgcaatgg cgtgatcact agttctaaac cggcgccaac    600
gcggtgggnc tccaattcc                                                   619

<210> SEQ ID NO 21
<211> LENGTH: 911
<212> TYPE: DNA
<213> ORGANISM: Homo sapiens

<400> SEQUENCE: 21
accacatcca gacaatgaga agccaaaacc ttcatccttc atgatttcct tagccctccc      60
taattcctat ttaccttggt gtagttacat tccttccctg ctgtataaac tcccaatttt     120
agtcagtaag ggagatggat ttgagataca tctcccaact ccttggcagc agcacctggt    180
taaagcctcc tttcctggca atactatagt ctcagtgatt ggctttcttt gtggtgagca     240
gcaggaccta gactgaaatt gtagtatttt ggtaacagta tctgctctcc attcaaatct     300
atgctcagcc atacagaatt attttttcag tttctttgaa tattctgcat attttcttct    360
acctctaagc ctccaaaaat aatctgaaaa gcagcaaaat cgccacaatg tggaatcaaa    420
ataggggtaa aaagccctt agacattctt ttggcaataa actaactgaa cttagtagga    480
cctggctcat agagacttct ctctttagga agtggacatc tggtgactca agcatttggc    540
ttgaagcagt tttcagggga gtttcaactg caattccaca ggatttcatt accagctatt    600
tgcggtcttg cttttcctt tgctggtact aaacaggtga catatatttt acattgataa     660
ttagtgtcat ctgacttgag gccactgctt tccttcttag tttctggtgc cctttgcagt    720
agtgcctttc ctaccatttt acatttggca gactggaaca gctcaaatag ctccaagaaa    780
```

```
gaaaaaactg cctcctttgt ctattcaagg ctctcacttc accttaaatg cagaatttt      840 tcttttcctt ttttttaag ttatgtatga ggattttttc ttttctttt tctttttga       900 gacagggtct t                                                          911
```

<210> SEQ ID NO 22
<211> LENGTH: 419
<212> TYPE: DNA
<213> ORGANISM: Homo sapiens
<220> FEATURE:
<221> NAME/KEY: misc_feature
<222> LOCATION: (120)..(298)
<223> OTHER INFORMATION: n = A, T, C, or G

<400> SEQUENCE: 22

```
acttgagtcc aggagttcaa ggctgtagtg agttgtgatt gcaccaccgc actccagcct      60
cgatgacaga gtgagaccct gtctgttaaa aataataat aataatagat aatgggatan      120
gagtgtaaag aaagacagga tgcttcttag caaagttaca aaaatatta atangtcttt      180 gtcacaaata tatgtttgcc tatgagctga aagagaaaa tgaaaagtg aaaataagat       240 ttctcaaggt acaactttga tgcagttcan gtcaaactta ngtaagattt tgttgtanag    300
tttgggaaat aaccattgtg gcaaggctgg aatgcaaatc gattttttgc tgttacagaa    360
acagtaaatg aatttatggg atttatttt aatttagtta gctttttatg aggagaatt     419
```

<210> SEQ ID NO 23
<211> LENGTH: 565
<212> TYPE: DNA
<213> ORGANISM: Homo sapiens

<400> SEQUENCE: 23

```
ataattccat tcgattccac tcgatgattc cattcgagtt cattgactgt tccattccat     60
tccattcgat gatttcattc gagtccactc gatgattcta ttcgattgca ttcgataatt    120
ccattcgttt gcattcgata attccattcg attccattgg aggataattc catttgagtc    180
cattcgatga ttgttccatt cgattctatt cggtgattcc attcgattcc atttgataat    240
gattccaatc gagaccattc gatgattcca ttcaattcca ttcaatcatg atcccttttcg  300 agtccattca atgattccat tccagtccat tcgatgattc catctgattc cattcaatga   360
atccattcga ttccattcta tgacgattcc attcatttca tctgatgatg attccattcg   420
attcattcag tgataccatt cgattcattc gatgatgatt caatcaattt aatcgatgat   480
tcattcgaat cattcgatga tgagtcatca tttcaattca tggtaattca ttcgtttcaa   540
tcgatggtgt tcatttgatc atcga                                           565
```

<210> SEQ ID NO 24
<211> LENGTH: 584
<212> TYPE: DNA
<213> ORGANISM: Homo sapiens
<220> FEATURE:
<221> NAME/KEY: misc_feature
<222> LOCATION: (328)..(582)
<223> OTHER INFORMATION: n = A, T, C, or G

<400> SEQUENCE: 24

```
agagcagtcc agtatatata catacatata caagctacaa gctgcatatg taatttaaaa     60
ttttctaata accacattta aaaggtaaa aagaaactgt tgaaataaat tttaatatct    120
ttcattgaac ccaatatatg caaaatacta tcatttcaat tataaccaaa ttaaaattaa    180
```

-continued

```
ggagatattt tacaattttc atattaacgt ttccaattct ggtgtgaatt ttacactcac       240
cgaacatctc aattctgaca agtcatattt taagtgctca acagctacgt gaggatagtg       300
gctattatgt cacaaaatgc agctctangg atgaggacag tttacagaag atacttgagg       360
atacaggagc aagttaaatg gcagtttaag aaagcaaatc cangatgtgg gaaactccac       420
agaatanatg acctggtttc tcccttcact catccctcca aaatagaaat caatggcaga       480
aagaaaaaag anggaggctg ttgtancata aaatacttag ggacatacaa taaaaacagt       540
gtagggtttt gttgaanccg attcactaca atgattcaca antt                       584
```

<210> SEQ ID NO 25
<211> LENGTH: 678
<212> TYPE: DNA
<213> ORGANISM: Homo sapiens
<220> FEATURE:
<221> NAME/KEY: misc_feature
<222> LOCATION: (5)..(675)
<223> OTHER INFORMATION: n = A, T, C, or G

<400> SEQUENCE: 25

```
ggggnnnntn tnnngnaaat ctctgngttc gggcccccc ancaaggtcg aggcctatcg        60
ataagctana tatcggaatt cctgcagccc ggggatctg atggttttat aaaggggagt       120
tgccctgcga aagctctctc ttacctgccg ccatgtaaga ccggactttg ctcctcatta      180 ggtcaccta gccatgtgga actgtgagtc cattaaacct ctttccttta taaattatgc      240
agtctcggat atgtctttat tagcaaggtg aaaatgaact aatacaaggg tcacgtggta      300
aatatattta atattaaaaa aaaatcttcc aaactatttt ccagagtgtc tgtacctttt     360
tacatttcca tgagcaacgt atgagtgatt tagtttcttt gacagcattt ggtatagtta      420
ctatttttta ttttagttgt tctcatcctg gacttaattt gaattttccc aatgatgagt      480
gatgttgaaa atttctttgt gcttacttgt catctggata ttctcgtcaa taaaatgtct      540
cttantatcn tttgcccatt tcaantgga ttcctttgt gttttatcat tgaattttaa        600
gaattcttcn atttatagat atgaattaca gatanaatca tagatattat agatanatat      660
gagttatggt tcacnatt                                                     678
```

<210> SEQ ID NO 26
<211> LENGTH: 508
<212> TYPE: PRT
<213> ORGANISM: Homo sapiens

<400> SEQUENCE: 26

```
Met Ala Ala Asp Ser Asp Asp Gly Ala Val Ser Ala Pro Ala Ala Ser
1               5                   10                  15

Asp Gly Gly Val Ser Lys Ser Thr Thr Ser Gly Glu Glu Leu Val Val
            20                  25                  30

Gln Val Pro Val Asp Val Gln Ser Asn Asn Phe Lys Glu Met Trp
        35                  40                  45

Pro Ser Leu Leu Ala Ile Lys Thr Ala Asn Phe Val Ala Val Asp Thr
    50                  55                  60

Glu Leu Ser Gly Leu Gly Asp Arg Lys Ser Leu Leu Asn Gln Cys Ile
65                  70                  75                  80

Glu Glu Arg Tyr Lys Ala Val Cys His Ala Ala Arg Thr Arg Ser Ile
                85                  90                  95

Leu Ser Leu Gly Leu Ala Cys Phe Lys Arg Gln Pro Asp Lys Gly Glu
            100                 105                 110
```

```
His Ser Tyr Leu Ala Gln Val Phe Asn Leu Thr Leu Leu Cys Met Glu
        115                 120                 125

Glu Tyr Val Ile Glu Pro Lys Ser Val Gln Phe Leu Ile Gln His Gly
130                 135                 140

Phe Asn Phe Asn Gln Gln Tyr Ala Gln Gly Ile Pro Tyr His Lys Gly
145                 150                 155                 160

Asn Asp Lys Gly Asp Glu Ser Gln Ser Gln Ser Val Arg Thr Leu Phe
                165                 170                 175

Leu Glu Leu Ile Arg Ala Arg Arg Pro Leu Val Leu His Asn Gly Leu
            180                 185                 190

Ile Asp Leu Val Phe Leu Tyr Gln Asn Phe Tyr Ala His Leu Pro Glu
        195                 200                 205

Ser Leu Gly Thr Phe Thr Ala Asp Leu Cys Glu Met Phe Pro Ala Gly
    210                 215                 220

Ile Tyr Asp Thr Lys Tyr Ala Ala Glu Phe His Ala Arg Phe Val Ala
225                 230                 235                 240

Ser Tyr Leu Glu Tyr Ala Phe Arg Lys Cys Glu Arg Glu Asn Gly Lys
                245                 250                 255

Gln Arg Ala Ala Gly Ser Pro His Leu Thr Leu Glu Phe Cys Asn Tyr
            260                 265                 270

Pro Ser Ser Met Arg Asp His Ile Asp Tyr Arg Cys Cys Leu Pro Pro
        275                 280                 285

Ala Thr His Arg Pro His Pro Thr Ser Ile Cys Asp Asn Phe Ser Ala
    290                 295                 300

Tyr Gly Trp Cys Pro Leu Gly Pro Gln Cys Pro Gln Ser His Asp Ile
305                 310                 315                 320

Asp Leu Ile Ile Asp Thr Asp Glu Ala Ala Glu Asp Lys Arg Arg
                325                 330                 335

Arg Arg Arg Arg Arg Glu Lys Arg Lys Arg Ala Leu Leu Asn Leu Pro
            340                 345                 350

Gly Thr Gln Thr Ser Gly Glu Ala Lys Asp Gly Pro Pro Lys Lys Gln
        355                 360                 365

Val Cys Gly Asp Ser Ile Lys Pro Glu Glu Thr Glu Gln Glu Val Ala
    370                 375                 380

Ala Asp Glu Thr Arg Asn Leu Pro His Ser Lys Gln Gly Asn Lys Asn
385                 390                 395                 400

Asp Leu Glu Met Gly Ile Lys Ala Ala Arg Pro Glu Ile Ala Asp Arg
                405                 410                 415

Ala Thr Ser Glu Val Pro Gly Ser Gln Ala Ser Pro Asn Pro Val Pro
            420                 425                 430

Gly Gly Gly Leu His Arg Ala Gly Phe Asp Ala Phe Met Thr Gly Tyr
        435                 440                 445

Val Met Ala Tyr Val Glu Val Ser Gln Gly Pro Gln Pro Cys Ser Ser
    450                 455                 460

Gly Pro Trp Leu Pro Glu Cys His Asn Lys Val Tyr Leu Ser Gly Lys
465                 470                 475                 480

Ala Val Pro Leu Thr Val Ala Lys Ser Gln Phe Ser Arg Ser Ser Lys
                485                 490                 495

Ala His Asn Gln Lys Met Lys Leu Thr Gly Ser Ser
            500                 505

<210> SEQ ID NO 27
<211> LENGTH: 3935
<212> TYPE: DNA
```

<213> ORGANISM: Homo sapiens

<400> SEQUENCE: 27

```
agcttatatt ctaatgggga cagaaaagga ataatgaaca taagtaaatt ccataagatg    60
ttaggtgata aatattagca taaaaagcaa aaattagacc aagagggaa aaaaaagagt    120
gccaaggtgg ggtttaatgt tgcaattta aagactgtgg tcaaggtaga cccaaagcat    180
tctaagtgag tgcaaaggcc ccaaggaggg tgcctggtat gtctgtggta cagtaagtag    240
gtcaatgtgg ttagaatgga atgagatggg actgagtggt agaagaggtc agagaagtaa    300
accagatgag gtggggagag gagggtcaca aagtacctta taggccattg gagggatttg    360
gctgccacac ccttgctctt agaaggcagt cctcttacta cagccttgca ggtccagtga    420
tccgggcacc atccgcctca tcccctcact atgctctagc caaggttgac tgaatttagt    480
tgcttaaaca cctcaagtgt gtctgcccac cttggggcct cacacaatcc atttcctctg    540
tttggactct tttatgcttt tacctaacac cttatcattt ttcaagtctt gactgaaatg    600
tccaaatcag gtcccctcat cttatcctat cacatatttc tgccttgtag ctcttaccta    660
atgtaatttt acattacttt gattctttcc atcagtgtgt acttcctgaa tttgactgta    720
aaaaacgact tgagtgcaag gactgattct cttgttgatt ggtgtgtgtc caaagtcagt    780
gccaggtaaa ctgtacacaa tagatacctg ttaaatgaat taatgggatg ggggatagtc    840
aaaagagttt cccttttta ggataggaga atccaaaga gtttttttat ttttgtttt    900
tttttgtttg tttgtttgt tttagagac agtgtgtccc tcacttgct gctctgccac    960
tcaggctgga gtgcaataag aacatggctc actgcagcct cgacctcctg ggctcaagcc   1020
atcctctcac ctcagcctcc tgtagctggg actacaggtg cgcaccacca tgcccaacta   1080
attttttaatt ttcttttgt agagacaagg tttcactatg ttgcccaggc tagtcttgaa   1140
ctcctagggt caagcgatcc tcccaccttg gcctcctaag atgattacag gcataagcc   1200
actgcgcccg gcccaagcag ttctgaataa tgatgaaatg ggctcagttg agagaagctg   1260
aagattaact ataaacaatg agtaacaaag gagcactgga aggcagaggt ggatgggaat   1320
cgtagtgttt acggagggac tagtctccaa taggaatttt tttttttttt tttttttttga   1380
gacggagttt cgctcttgtt gcctaggctg aagtgcaaaa tggcgtgatc tcggctcacc   1440
gcaacctctg cctcccaggt tcaagcgatt ctcctgcctc agcctcccaa gtagtgggat   1500
tacaggcgcc cgcaccatac ccagctaatt ttttttgtac ttttagtaga cgggggttt   1560
caccatgttg gccaggctgg ttttgaactc cggacctcag gtaatccgcc cgcctcggcc   1620
tcccaaagtg ctgggattac aggcgtgagc caccgcgccc ggcctaggaa cctctttcaa   1680
attcaatcac cctctaggtc gactataccg cctagctgct tcacaatttg tcccttcctc   1740
gccatccata ctgccagcct taattcaagt tcacattatc acttgattgg attattacaa   1800
aagcttccct accaatcggt cgctcttaca ccctgggcag cctcctccga tggcccactc   1860
cccgcctctt tcactttctg gagatcactg agctctccat cctctctggg aatttaccga   1920
tgcccagaac gccttcttt ccccacacg accctctcct agtctaactc ctgggcgtgc   1980
tttaagctca gctcaggcag cgtcaccttc tctggaaagc ccaaacccag ccaccccact   2040
acccgctacc cgcggcccac gctgatgaag acagcagaac acgaggcccc cgcgttcccg   2100
ccgcgagagc aggagagaaa gattacctcc cgcgagctct agcgcgcccg gctttccggc   2160
gcactccagg gggcgtggct cgggtccacc cgggctgcga gccggcagca caggccaata   2220
ggcaattagc gcgcgccagg ctgccttccc cgcgccggac ccgggacgtc tgaacggaag   2280
```

-continued

```
ttcgacccat cggcgacccg acggcgagac cccgccccat ccccgactgc ctgaaccgcg    2340
ccaggagacg gaccgcaagt ccagcgtacc cacagacgac tcaggcggga gacgagcggt    2400
gtcatggccg ccgacagtga cgatggcgca gtttcagctc ccgcagcttc cgacggtggt    2460
gtcagcaaaa gcacaacatc tgggaggagc tagtagtcca ggttcccgta gtggatgtgc    2520
aaagcaacaa cttcaaggag atgtggccat ccctcctgct agccataaag acagctaatt    2580
tcgtggctgt ggacacggag ctgagtgggc ttggggacag gaagagtttg ctgaaccagt    2640
gcattgagga acgttacaag gccgtgtgtc atgctgccag gacccgttct atcctttccc    2700
tgggcctcgc ctgcttcaag cggcagccag acaagggtga acattcctat ctggctcaag    2760
tgttcaatct cactctgctg tgcatggagg agtatgtcat agaaccaaag tctgtgcagt    2820
tcctgataca gcatggcttc aacttcaacc agcagtatgc ccaaggcatc ccctaccata    2880
agggcaatga caagggtgat gagagccaga gccagtcagt acggacccta ttcctggagc    2940
taatccgagc ccgccggccc ctggtgctac acaatggcct tatagacttg gtgttcctgt    3000
accagaactt ctatgcacac ctccctgaga gtctgggaac cttcaccgct gacctgtgtg    3060
agatgttccc agcaggcatt tatgacacca aatatgctgc tgagtttcat gcccgtttcg    3120
tggcctccta cttagaatat gccttccgga aatgtgaacg ggaaaatggg aagcagcggg    3180
cagctggcag cccacacctt accctggagt tctgcaacta tccttccagc atgagggacc    3240
atattgatta ccgctgctgc ctgccccag caacccaccg tcctcatccc accagcatct    3300
gtgacaactt ctcggcttat ggctggtgcc cctgggacc acagtgtcct cagtctcacg    3360
atattgacct tatcattgac actgatgagg ctgcggcaga ggacaagcgg cgacggcgac    3420
gacgtaggga aaaacggaag agggctttat tgaacctacc ggggacacag acctctgggg    3480
aagctaagga tggtcctccc aagaagcagg tctgtgggga tagcatcaag cctgaagaaa    3540
ccgagcagga ggtggctgcc gatgaaacta ggaacctgcc tcactccaag caaggcaaca    3600
aaaatgactt agagatgggg attaaggcag caaggcctga aatagctgat agagctacct    3660
cagaagtgcc agggagccaa gccagtccta acccagtgcc tgggggtgga ttgcaccggg    3720
ctggttttga tgcctttatg acaggttatg tgatggccta tgtggaagtg agccagggac    3780
cgcaaccctg cagctctgga ccctggctcc ctgaatgcca caataaggta tatttgagtg    3840
gcaaagctgt acccctcaca gtggccaaga gccagttctc tcgttcctcc aaagcccaca    3900
atcagaagat gaagctcact tggggcagta gctga                              3935
```